United States Patent
Muhammed et al.

(10) Patent No.: US 7,835,002 B2
(45) Date of Patent: Nov. 16, 2010

(54) SYSTEM FOR MULTI- AND HYPERSPECTRAL IMAGING

(75) Inventors: Hamed Hamid Muhammed, Uppsala (SE); Fredrik Bergholm, Nynäshamn (SE)

(73) Assignee: RP Ventures Technology Office AB, Stockholm (SE)

( * ) Notice: Subject to any disclaimer, the term of this patent is extended or adjusted under 35 U.S.C. 154(b) by 618 days.

(21) Appl. No.: 11/577,860

(22) PCT Filed: Oct. 25, 2005

(86) PCT No.: PCT/SE2005/001607

§ 371 (c)(1),
(2), (4) Date: Nov. 30, 2007

(87) PCT Pub. No.: WO2006/046913

PCT Pub. Date: May 4, 2006

(65) Prior Publication Data

US 2008/0123097 A1    May 29, 2008

(30) Foreign Application Priority Data

Oct. 25, 2004    (SE) .................................. 0402576

(51) Int. Cl.
*G01N 21/25*    (2006.01)
(52) U.S. Cl. .................... 356/419; 356/418; 250/226
(58) Field of Classification Search .................. 356/416, 356/418–419; 250/226; 348/294–326, 335–336, 348/340, 342; 359/634
See application file for complete search history.

(56) References Cited

U.S. PATENT DOCUMENTS

| 4,513,312 | A | * | 4/1985 | Takemura | .................... 348/275 |
| 4,764,670 | A | * | 8/1988 | Pace et al. | .................. 250/226 |
| 5,483,379 | A | * | 1/1996 | Svanberg et al. | ............. 359/634 |
| 5,729,011 | A | * | 3/1998 | Sekiguchi | .................... 250/226 |
| 5,926,283 | A | | 7/1999 | Hopkins | ...................... 356/419 |
| 5,929,432 | A | * | 7/1999 | Yamakawa | ................. 250/208.1 |
| 5,982,497 | A | | 11/1999 | Hopkins | .................... 356/419 |
| 7,474,402 | B2 | * | 1/2009 | Shannon et al. | ............. 356/405 |
| 2003/0198364 | A1 | | 10/2003 | Yonover et al. | ............. 382/103 |

* cited by examiner

*Primary Examiner*—Tarifur Chowdhury
*Assistant Examiner*—Michael LaPage
(74) *Attorney, Agent, or Firm*—Greenberg Traurig LLP

(57) ABSTRACT

Arrangement for the production of instantaneous or non-instantaneous multi-band images, to be transformed into multi- or hyperspectral images, comprising light collecting means, an image sensor array, and an instantaneous colour separating means, positioned before the image sensor array, and uniform spectral filters, for restricting imaging to certain parts of the electromagnetic spectrum. A filter unit is positioned before the colour separating means in the optical path in, or close to, converged light. Each filter mosaic consists of a multitude of homogeneous filtering regions. The transmission curves of the filtering regions of a colour or spectral filter mosaic can be partly overlapping, in addition to overlap between these transmission curves and those belonging to the filtering regions of the colour separating means. The transmission curves of the colour or spectral filter mosaics and the colour separating means are suitably spread out in the intervals of a spectrum to be studied.

27 Claims, 21 Drawing Sheets

| CR | CG | R | G |
|----|----|----|----|
| C | CB | T | B |
| YR | YG | MR | MG |
| Y | YB | M | MB |

| CR | CG | R  | G  | CR | CG | R  | G  |
|----|----|----|----|----|----|----|----|
| C  | CB | T  | B  | C  | CB | T  | B  |
| YR | YG | MR | MG | YR | YG | MR | MG |
| Y  | YB | M  | MB | Y  | YB | M  | MB |
| CR | CG | R  | G  | CR | CG | R  | G  |
| C  | CB | T  | B  | C  | CB | T  | B  |
| YR | YG | MR | MG | YR | YG | MR | MG |
| Y  | YB | M  | MB | Y  | YB | M  | MB |

Fig.28

SYSTEM FOR MULTI- AND HYPERSPECTRAL IMAGING

FIELD OF INVENTION

The present invention relates to a system comprising an arrangement and a method for the production of spectral-information-rich multi-band images and also multi- and hyperspectral images, or production of spectra or spectral-information-rich signals in general. The arrangement comprises light collecting means, an image sensor with at least one two dimensional sensor array including an embedded (integrated with the image sensor) colour separating means, and an optional uniform spectral filter in the optical path of the arrangement, with the purpose of restricting imaging to certain parts of the electromagnetic spectrum. The present invention also relates to an optical auxiliary device and a method for generating multi- and hyperspectral images. Colour mosaics, uniform colour filters and/or colour filter wheels may be included in an inventive arrangement or inventive optical auxiliary device. The image, registered by the image sensor, is demosaicked into a multi-band image where each band consists of pixels registering a specific filter's response signals. Empty areas in each band are filled using interpolation. A spectrum is estimated for each multi-band pixel, and consequently, a multi- or hyperspectral image is obtained. It is of course possible to generate one spectrum for the whole imaged scene by computing the mean of all spectra in the resulting image, but a more efficient approach is to compute the mean value of each band (or of a certain portion of each band) of the multi-band image, and finally transform the resulting multi-band vector into a spectrum, i.e. a spectrometer is obtained. Optical fibres can be used to guide the light to a certain part of the image sensor array, and consequently obtain a multi-spectrometer that can measure, in parallel, as many light sources as the number of used optical fibres. Instantaneous multi- and hyperspectral images are obtained when no colour-filter wheels, or other means for filter interchange or exchange, are included in the arrangement. Filter interchange or exchange can be performed by using any filter holders with moving parts, and also by using flat thin transmissive displays to display a sequence of required uniform colour filters and/or filter mosaics.

DESCRIPTION OF THE BACKGROUND ART

Despite an impressive evolution of multi- and hyperspectral sensors, usually called spectrometers, there are still very few or crude ways of obtaining an instantaneous so-called multi- or hyperspectral 2D-image of the environment; i.e. 2D-images with more than three spectral bands. We define a hyperspectral image as an image containing more than ten spectral bands, while a multispectral image has between four and ten bands.

Today's multi- and hyperspectral sensor systems are dependent on spatial and/or spectral scanning to produce the resulting image. Some of these systems are described in the publications:

"Photodiode array Fourier transform spectrometer with improved dynamic range" by T. H. Barnes in Appl. Opt. 24, 3702-3706 (1985), "Fourier Transform Spectrometer with a Self-scanning Photodiode Array" by T. Okamoto, S. Kawata and S. Minani in Appl. Opt. 23, 269 (1984), "THRIFTI: tomographic hyperspectral remote imaging Fourier transform interferometer" by Slough, W., J.,
Rafert, J. B., Rohde, C. A., Hart, C. L., in the Proceedings SPIE Vol. 3393, 207-216, (1998), "A Visible, Spatially-Modulated Imaging Fourier Transform Spectrometer (SMIFTS) for Astronomical Applications" by Rafert, J. B., Holbert, E. T., Rusk, E. T., Durham, S. E., Caudill, E., Keating, D., Newby, H. in the Bulletin of the American Astronomical Society, 24, 1282, (1992), and "Polarization interferometer for visible Fourier transform spectrometer of static type" by Tugbayev, V. A. in Proceedings SPIE Vol. 2089, 292, (1994).

In the case of spatial scanning the sensor system captures whole spectra instantaneously, but only for a small region of the scene at each instant of time, and spatial scanning is used to cover the whole scene. This can be achieved by, for example, using a line of sensor elements translated across the scene to be imaged, which is the way most multi- and hyperspectral images are generated, cf. aerial and satellite images as well as in industrial inspection. The converse holds for spectral scanning, thus requiring time to obtain complete spectra. Spectral scanning can be achieved by, for instance, using a filter wheel containing a number of different narrow or broad band filters, and exactly the same scene must be registered using each of these filters.

A disadvantage associated with the need of scanning procedures, is that the resulting image is sensitive to changes in the scene faster than the scanning time. This is in particular severe for close range imaging for fast varying events. The present invention aims at capturing instantaneous multi- and hyperspectral 2D-images when no filter interchange or exchange is performed, i.e. no spectral scanning of the scene is required.

Digital colour cameras can produce instantaneous RGB (Red, Green, Blue) colour images, using colour filter mosaics (e.g. the Bayer colour filter array) integrated with the image sensor chip. The used colour filter mosaics may consist of RGB, RGBE (E=Emerald), CMY (Cyan, Magenta, Yellow) or CMYG colour regions. Processing the responses of the sensors behind the different coloured regions of the used mosaic produces the final RGB image.

In other words, three or four broad-spectral-band filters are used to produce an RGB image; a 3-colour-bands image. An extension to this technique can be the use of a number of high quality narrow band filter mosaics to produce an image with as many bands as the number of the different filters used in the mosaic, cf. U.S. Pat. No. 4,885,634 showing an endoscope for display of monochrome and colour images, where an optical endoscope is connected to a TV camera and an image signal processor for specific spectral-wavelength components, and display means for a monochrome image with respect to a specific wavelength region along with a normal colour image. However, the high cost of this approach limits its usefulness.

Publication "Static polarization interference imaging spectrometer (SPIIS)" by Zhang, C., Bin, X., Zhao, B., in Proceedings SPIE Vol. 4087, p. 957, (2000), teaches a new technology in development that can be used for instantaneous hyperspectral imaging.

SUMMARY OF THE PRESENT INVENTION

The present invention teaches the use of a number of overlapping broad spectral-band filters to produce (after appropriate image demosaicking and processing) a spectral-information-rich multi-band image that can be transformed into a multi- or hyperspectral image with a number of narrow spectral bands. A series of overlapping filters (these filters are positioned either in direct physical contact or in different places in the optical path of the arrangement) build a so-called multiple filter, i.e. the incoming light goes through the constituent filter layers in succession. A number of low-cost colour filters can be used to build multiple filters which are equivalent to using a larger number of high-cost narrow band filters. Consequently, the spectral-scanning time is reduced when using these multiple filters instead of the corresponding narrow band filters (note that each filter must cover the whole scene). Furthermore, it is possible to totally eliminate the scanning time by constructing a high-resolution mosaic of these multiple filters (using a periodic pattern consisting of these filters). Another possible way to achieve this goal is by using multi-chip sensors, requiring complicated and costly optical as well as electronic hardware.

In a digital colour camera, the manufacturer has already put in a colour mosaic (e.g. the Bayer colour filter array), integrated with the sensor, and it is very difficult and costly to replace or change these filters. Therefore, there is a need for a cost-effective flexible device yielding instantaneous multi- or hyperspectral 2D images or instantaneous multi-band images containing more spectral information than the corresponding colour images.

One proposed embodiment of the present invention teaches the use of a digital colour camera (comprising a CCD or a CMOS image sensor chip) with an additional lens system with colour mosaic(s) in the optical path, for the purpose of acquiring instantaneous 2D images with many spectral bands. By disposing the filter layers in the optical path, this is made possible. It is also cost efficient.

Another approach is to cover the image sensor chip (that may already have an own embedded colour filter mosaic) with a thin multiple filter mosaic film, either as a loosely-placed thin film (or stack of thin films, i.e. a block of sandwiched thin films) covering the image sensor elements, or as a layer integrated (embedded) with the image sensor elements. Direct contact between the image sensor elements and the covering film or layer must be achieved to guarantee placing this extra film or layer in converged light in the optical path. Micro-lenses can be used to provide converged light for the film and the sensors.

If scanning time is not critical (no movements or changes occur, neither regarding the camera position nor the scene, when acquiring the image cube), it is also possible to obtain multiple filters by using a number of overlapping filter wheels aligned and positioned in converged light in the optical path; that is the window, of each filter wheel through which the current uniform colour filter appears, is positioned in converged light in the optical path. Exactly the same scene is registered using the different multiple filters produced by selecting different combinations of the uniform colour filters mounted on the filter wheels. Combination of uniform-colour-filter wheels (equivalent to using interchangeable uniform colour filters) and fixed colour filter mosaics can also be utilised to produce multiple filter mosaics. A more general approach is to combine uniform-colour-filter wheels with colour-mosaic-filter wheels (equivalent to using interchangeable colour filter mosaics). Using moving parts yields non-instantaneous imaging systems. It is also possible to use flat thin transmissive displays to function as filter interchange or exchange devices. At any instance of time, required uniform colour filters or colour filter mosaics are simply displayed by these displays. Filter interchange during image-cube registration yields a non-instantaneous image, while filter exchange between different image registration tasks can be used to change the wavelength rage of the system and optimise it for different applications.

Another more costly instantaneous imaging approach is using multi-chip cameras (e.g. a 3-chip camera) where it is possible to combine uniform colour filters with colour filter mosaics to produce multiple filter mosaics.

The invention is an imaging system for the purpose of generating spectral-information-rich multi-band images as well as multi- and hyperspectral 2D images, constructed so as to produce combinations of transmission filters (referred to as multiple filters) in the optical path by the use of overlapping colour filters and/or colour filter mosaics. The used filters or mosaics may be produced by ordinary printing techniques, normally yielding broad band colour filters, with a moderate quality when considering transparency. However, placing these filters in converged light in the optical path compensates for these imperfections. Of course, conventional transmission filters and filter mosaics, sensitive to visible and/or near-infrared light, can also be utilised. Light rays pass through the whole optical system penetrating the overlapping colour filters (can be small homogenous colour areas in colour filter mosaics), successively.

Ordinary printing techniques yield useful colour filters and colour filter mosaics when placed in converged light in the optical path (within an optical lens system and/or directly covering the image sensor elements). This makes the filtering part of an inventive system cost efficient.

The invention also shows how to construct the additional multiple filter mosaic as a separate module, so that for example a lens system with this mosaic can easily be attached to an ordinary digital camera, monochrome or colour camera, with or without own (embedded) camera lens. Having an ocular-equipped lens system to attach does this in case the camera already has a fixed (embedded) camera lens. Otherwise, if the camera doesn't have own (embedded) camera lens, the lens system functions as a camera lens equipped with colour filter mosaics. According to proposed embodiments, such lens system can then be considered as a lens accessory to a conventional digital camera, with or without own fixed (embedded) camera lens. Other proposed embodiments teach the use of filter wheels to hold uniform colour filters and/or colour filter mosaics (equivalent to using interchangeable filters and mosaics). Of course, it is possible to use flat thin transmissive displays, such as LCD, plasma or electrochromic displays, to function as uniform colour filters and/or colour filter mosaics, by simply displaying the required colour picture. These displays can be used instead of the filter wheels. However, new designs of these types of displays are needed to enhance their transparency and spectral characteristics.

The invention also aims at producing spectra in the final resulting image by a demosaicking and interpolation method followed by a transformation method, applied to the output image from the imaging part of the system. This transformation method takes as input, broad-band colour mosaic element responses and converts these signals by the use of e.g. linear algebra into approximate element-wise spectra. This makes the inventive system capable of producing instantaneous 2D images with spectra in pixels. No (spectral) scanning is needed if the system doesn't comprise flat transmissive displays (LCD, plasma or electrochromic), filter wheels or other filter holders with moving parts to be able to interchangeably use a number of different uniform colour filters and/or colour filter mosaics. Flat transmissive displays, filter wheels and the like are used to achieve better spatial and spectral resolution, but the system then acquires non-instantaneous images, because a series of images are needed to be registered using the different multiple filters. On the other hand, in the case of using fixed multiple filter mosaics (can be also shown on transmissive displays) only one image (that has the same size as the image sensor array) is registered, yielding reduction in spatial resolution of the resulting instantaneous multi- or hyperspectral image. To enhance the spatial and spectral resolution of the resulting instantaneous multi- or hyperspectral image, a more expensive approach can be used, utilising multi-chip image sensor (e.g. 3-chip image sensor) where combinations of uniform colour filters and/or colour filter mosaics can be used.

Using flat transmissive displays (LCD, plasma or electrochromic) makes it possible to use different colour filter mosaics optimised for different wavelength intervals.

The list of applications where multi- and hyperspectral imaging, using the inventive technique presented here, can be useful is rather long including (but not limited to) the following areas:

Precision agriculture/farming (monitoring soil conditions, predicting yield, plant identification, etc.).

Plant pathological stress detection and characterisation (detecting disease or pest infestation).

Veterinary (medical diagnoses, condition estimation, etc.).

Food quality inspection (inspection and sorting of fresh fruits and vegetables, milk and oil quality inspection, poultry, fish and meat quality inspection, fat estimation in meat, etc.).

Forestry, vegetation and canopy studies (mapping tree species, tree volume/size/age estimation, detecting damaged/broken trees, foreign body detection, etc.).

Eco system monitoring.

Environmental (wetlands, land cover, hydrology, etc.).

Plume detection and analysis.

Water quality and coral reefs monitoring.

Littoral studies (bathymetry, water clarity, etc.).

Health care (food safety, medical diagnoses e.g. melanoma detection and skin wound analysis, etc.).

Biological and chemical detection (detecting and identifying hazardous materials).

Material identification (natural and man-made materials).

Mineral exploration and mapping.

Camouflage and concealment detection.

Disaster mitigation.

City planning and real estate.

Traffic ability analysis.

Law enforcement (measuring spill extent and pollutants, tracking discharges of chemicals or oil, detecting illegal activities in protected areas, etc.).

However, it is obvious that the multi-band image (obtained after the demosaicking step) and the corresponding multi- or hyperspectral image (obtained after the transformation step) contain the same amount of spectral information. Hence, it is not necessary to convert the multi-band image into a multi- or hyperspectral image to be able to analyse the imaged scene. The analysis can directly be performed on the multi-band image yielding better performance than when using the estimated (i.e. introducing estimation error) multi- or hyperspectral image.

ADVANTAGES

The advantages of the present invention are that it enables the possibility to produce cost effective, instantaneous and non-instantaneous multi- and hyperspectral images or spectral-information-rich multi-band images using low-cost conventional camera and optical accessories.

BRIEF DESCRIPTION OF THE DRAWINGS

A system including an arrangement and a method according to the present invention will now be described in detail with reference to the accompanying drawings, in which:

FIG. 6 is a schematic and simplified illustration of the resulting multiple filter mosaic when using the colour filter mosaics in FIG. 4a.

FIG. 7 is a schematic and simplified illustration of a multiple filter mosaic where element-wise matching is achieved between the image sensor array and an RGBT mosaic, while a lower-resolution CMYT mosaic with randomly distributed random-shape colour elements is overlapping the RGBT mosaic.

In FIG. 25, filters with the transmission curves TC2 and TC4 can approximate filters with TC1, TC3 and TC5. In FIG. 26, filters with TC7 and TC8 can approximate filters with TC6, TC9 and TC10. In FIG. 27, filters with TC12 and TC13 can approximate filters with TC11 and TC14.

FIG. 28 is a schematic and simplified illustration of a multiple filter mosaic consisting of four mosaic units of the type presented in FIG. 6.

DESCRIPTION OF EMBODIMENTS AS PRESENTLY PREFERRED

Figure 1:
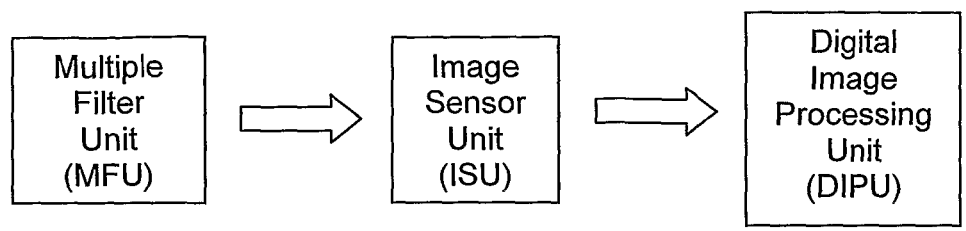
FIG. 1 is a schematic and simplified illustration of a system for the production of instantaneous and/or non-instantaneous multi- and hyperspectral images.

With reference to FIG. 1 a system for the production of instantaneous and/or non-instantaneous multi- and hyperspectral images will now be described.

The multiple filter unit (MFU) comprises multiple filter mosaics and/or uniform multiple filters placed in converged light in the optical path. A multiple filter is produced by stacking a number of optical filters either by placing them in different places in converged light in the optical path and/or stacking a number of them together (to get a block of sandwiched filters) and putting them in converged light. It is also possible to stack all of them together (and get a block of sandwiched filters) and putting them in converged light in the optical path, e.g. positioned directly on the image sensor elements where incoming light is received. Uniform multiple filters (e.g. for the purpose of non-instantaneous multi- and hyperspectral image registration) can be produced by overlapping uniform colour filters, while multiple filter mosaics (e.g. for the purpose of instantaneous multi- and hyperspectral image registration) can be produced by overlapping colour filter mosaics as well as uniform colour filters. These filters and mosaics can be mounted either in fixed filter holders or in filter wheels or other types of filter holders to be able to achieve a variety of filter combinations generating different multiple filters and mosaics. A flat thin transmissive display can be used to function as a colour filter mosaic or a uniform colour filter. It is also possible to interchange or exchange uniform filters and mosaics by displaying different colour patterns.

The image sensor unit (ISU) converts incoming light into electric signals and produces digital values corresponding to the sensed signals (usually by using A/D converters). The output of this unit depends on embedded functionality, so that the resulting output can either be one (single band) or three (Red, Green and Blue bands) 2D-arrays of digital values.

The digital image processing unit (DIPU) produces spectra in the final resulting image by an optional (if needed) demosaicking and interpolation method followed by a transformation-into-spectra method, applied to the output of the image sensor unit (ISU). The transformation method takes as input, multiple filter responses and converts these signals by the use of e.g. linear algebra into approximate spectra. This makes the inventive system capable of producing 2D images with spectra in the pixels. If multiple filter mosaics are utilised, then a demosaicking method and an optional (if required) interpolation method must be employed and instantaneous multi-band images are obtained. These multi-band images are finally transformed into multi- or hyperspectral images.

Figure 2:
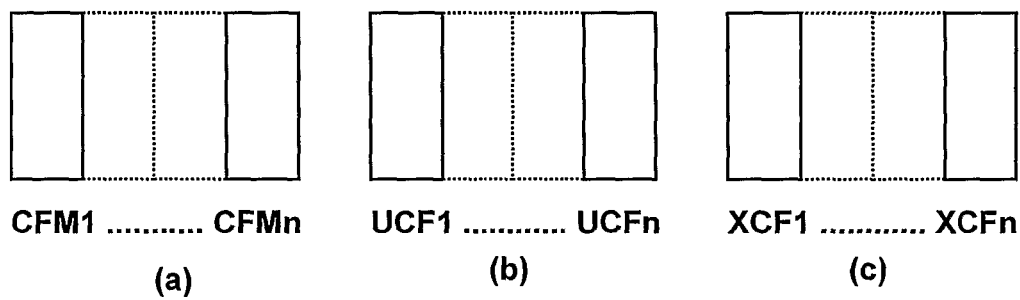
FIG. 2a is a schematic and simplified illustration of a filter unit (FU) consisting of overlapping colour filter mosaics, where CFMi refers to colour filter mosaic No. "i".
FIG. 2b is a schematic and simplified illustration of a filter unit (FU) consisting of overlapping uniform colour filters, where UCFi refers to uniform colour filter No. "i".
FIG. 2c is a schematic and simplified illustration of a filter unit (FU) consisting of overlapping uniform colour filters and colour filter mosaics, where an XCFi can be a CFMi or a UCFi.

FIG. 2 teaches that a filter unit (FU) is defined as overlapping colour filter mosaics, overlapping uniform colour filters, or overlapping uniform colour filters and colour filter mosaics, as illustrated by FIG. 2a, FIG. 2b and FIG. 2c, respectively, where CFMi and UCFi refer to colour filter mosaic No. "i", and uniform colour filter No. "i", respectively, while an XCFi can be a CFMi or a UCFi. A number (n≧1) of filters (CFMs and/or UCFs) are stacked together to build a filter unit (FU) (a block of sandwiched filters) to be used in the multiple filter unit (MFU) of the system. This means that a FU can also be a single CFM or UCF.

Figure 3:
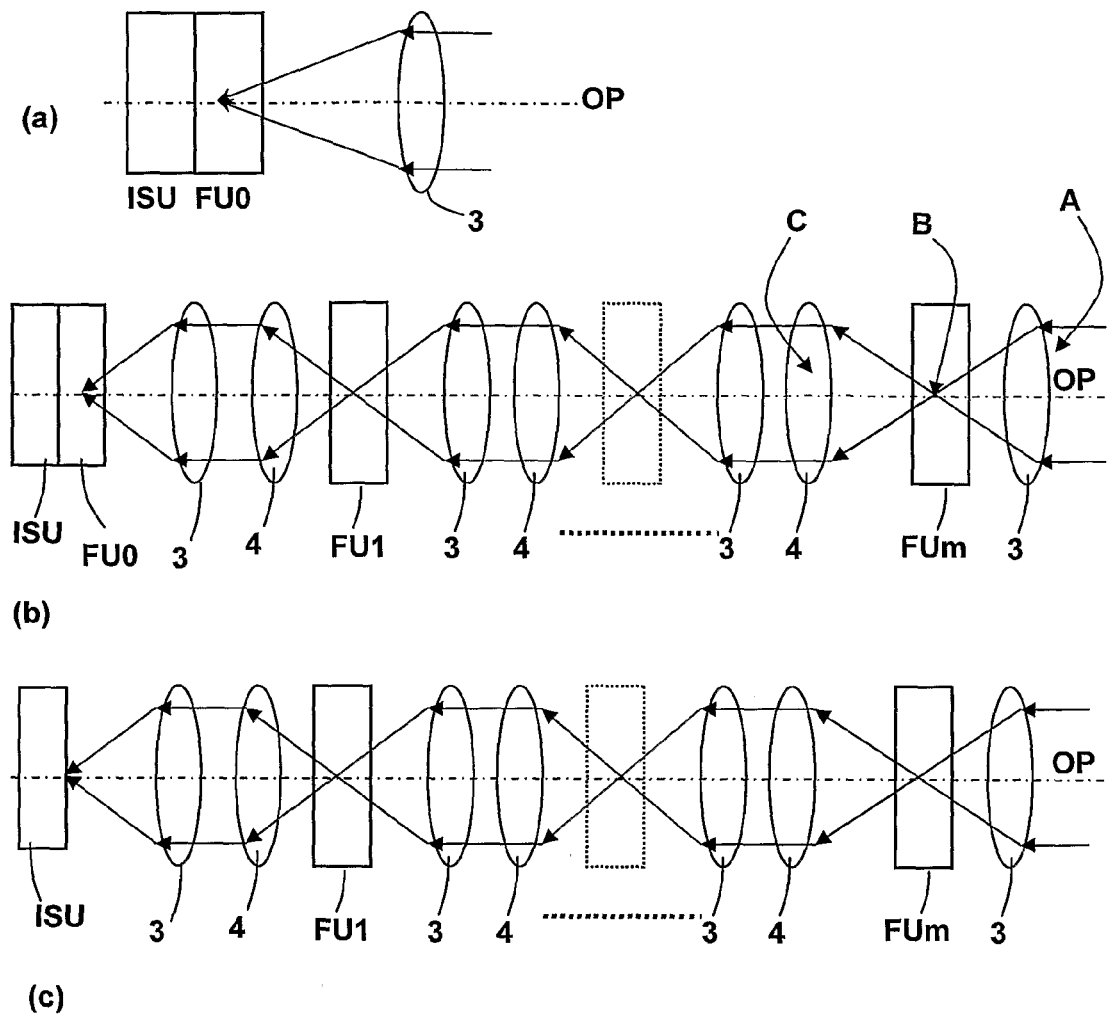
FIG. 3a is a schematic and simplified illustration of an arrangement for combining an image sensor unit (ISU) with a multiple filter unit (MFU) comprising a filter unit FU0 directly attached to the ISU.
FIG. 3b is a schematic and simplified illustration of an arrangement for combining an image sensor unit (ISU) with a multiple filter unit (MFU) comprising a filter unit FU0 directly attached to the ISU, in addition to a number ($m \geq 1$) of filter units (FUi) positioned in converged light in the optical path (OP).
FIG. 3c is a schematic and simplified illustration of an arrangement for combining an image sensor unit (ISU) with a multiple filter unit (MFU) consisting of a number ($m \geq 1$) of filter units (FUi) positioned in converged light in the optical path (OP). Note that no FU0 is used.

With reference to FIG. 3, three arrangements for combining an image sensor unit (ISU) with a multiple filter unit (MFU) are proposed, where FUi refers to filter unit No. "i" in the system. FU0, utilised in FIG. 3a and FIG. 3b, is a filter unit directly attached to the image sensor unit (ISU) and some of its constituent components (as illustrated in FIG. 2) can be integrated with the sensor chip (by the chip manufacturer), while the rest of the components (if any) can be mounted, either loosely or permanently, to cover the sensing elements on the chip. Note that the image sensor elements are positioned in converged light in the optical path (OP). FIG. 3a teaches that the multiple filter unit (MFU) can be made of only FU0, while in FIG. 3b in addition to using FU0, a number (m≧1) of filter units (FUi) are positioned in converged light in the optical path (OP). In FIG. 3c, filter units (FUi) are positioned in converged light in the optical path (OP), but no FU0 is used. In the multiple filter unit (MFU), as illustrated in FIG. 3, the optical system comprises any lenses (3) and/or mirrors required to focus incoming light (A) into converged light (B), and any lenses (4) and/or mirrors required to convert converged light (B) into outgoing approximately collimated light (C). All used lenses (3 and 4) and mirrors must be accurately aligned along the common optical path (OP) in the optical system.

An additional filter unit (FUi, i≧1), as illustrated by FIG. 3, can be either loosely or permanently mounted into either a fixed filter holder, or a filter wheel or other filter holder with moving parts to exchangeably use different filters (the window where the chosen filter appears must be aligned along the common optical path OP of the optical system). It is also possible to use a flat thin transmissive display as a colour filter mosaic or a uniform colour filter or to exchangeably show different filters or mosaics.

RGB, RGBE, CMY, or CMYG colour filter arrays are often integrated into the image sensors used for RGB colour image registration. This means that essential technology and dyes are available to be able to produce the filter unit FU0, illustrated in FIG. 3, by overlapping two colour filter mosaics consisting of complementary colours to achieve an image sensor that can register more spectral information than conventional colour image sensors. On the other hand, new designs are required to produce flat thin transmissive displays with enhanced transparency and spectral characteristics.

Figure 4:
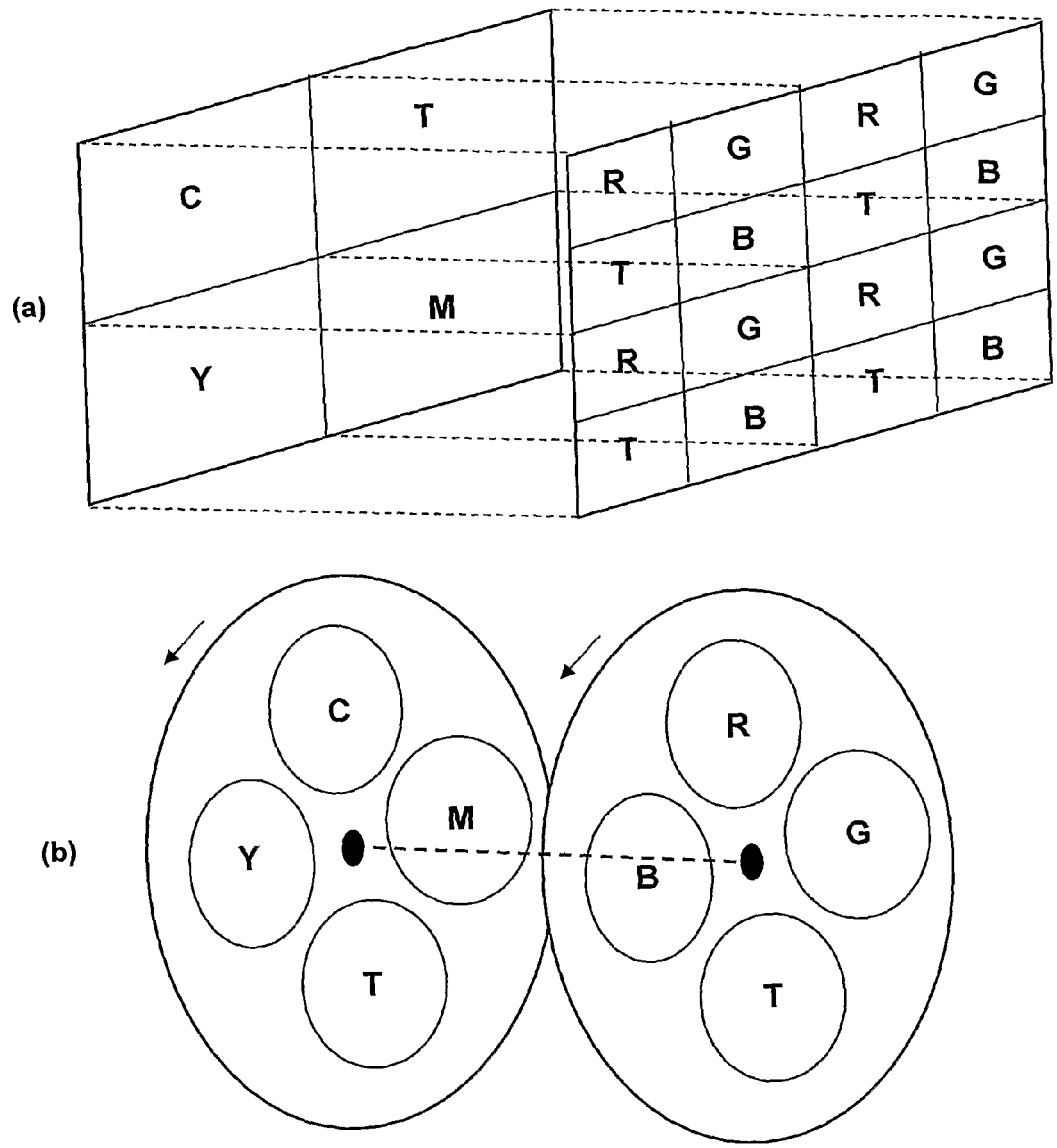
FIG. 4a is a schematic and simplified illustration of a multiple filter mosaic unit (that is repeated to form a mosaic covering the whole image sensor array) consisting of two overlapping colour filter mosaics, CMYT (consisting of Cyan, Magenta, Yellow and Transparent areas) and RGBT (consisting of Red, Green, Blue and Transparent areas), where each element of the CMYT mosaic covers 2×2 elements of the RGBT mosaic.
FIG. 4b is a schematic and simplified illustration of an arrangement for generation of uniform multiple filters, using two aligned filter wheels (the windows where the chosen filters, from each filter-wheel, appear must be aligned) holding uniform colour filters. Different combinations of filters from these two filter wheels produces different multiple filters.
Figure 5:
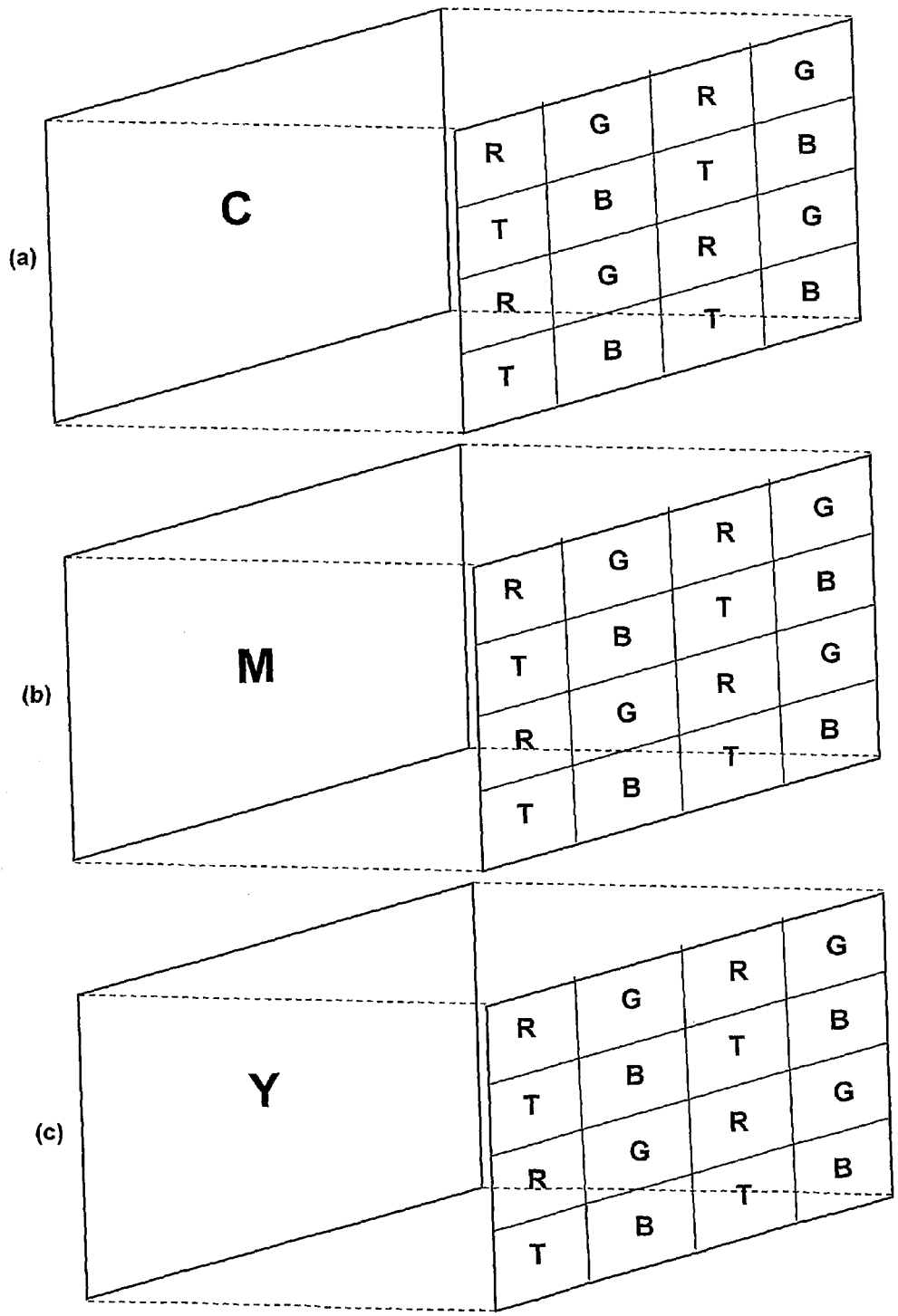
FIGS. 5a, 5b and 5c are schematic and simplified illustrations of three multiple filter mosaics to be used with a multi-chip image sensor, where each of these multiple filter mosaics covers one of the sensor arrays of the image sensor.

There are, virtually, infinitely many possible colour mosaic patterns. However, one preferred embodiment for instantaneous imaging would use overlapping CMYT and RGBT colour mosaics according to FIG. 4a, where element-wise matching is achieved between the image sensor elements and the R, G, B and T areas of the RGBT colour mosaic (each colour area covers exactly one sensor element). FIG. 4b shows the corresponding non-instantaneous approach using two filter wheels, while FIG. 5 illustrates the corresponding instantaneous 4-chip approach, where the fourth sensor array (not shown in the figure) is covered by the RGBT colour mosaic only. Here also, element wise matching is assumed being possible between the RGBT colour mosaic and the sensor array. Consequently, in FIGS. 4 and 5, each element of the CMYT colour mosaic covers 2×2 elements of the RGBT colour mosaic. Equivalent result is obtained when the spatial resolution of the CMYT colour mosaic is higher than the spatial resolution of the RGBT colour mosaic. This is achieved by exchanging the colours R, G and B by M, Y and C, respectively, in FIGS. 4 and 5. Here, element wise matching is assumed being possible between the CMYT colour mosaic and the sensor array. Consequently, each element of the RGBT colour mosaic covers 2×2 elements of the CMYT colour mosaic.

But, if element wise matching (between the higher resolution mosaic and the sensor array and/or between the higher resolution mosaic and the lower resolution mosaic) can not be achieved, then each higher-resolution-mosaic element should completely cover at least one sensor-array element, and each lower-resolution-mosaic element should completely cover one of each of the different elements of the higher resolution mosaic.

In general, in conjunction with available integrated image-sensor colour filter mosaics, the additional colour filter mosaics may contain both complementary colours to the colours of the integrated filters, and other colour or spectral filters. In addition to that, each element of the additional colour filter mosaic must cover at least one colour element of each of the different elements of the integrated colour filter mosaic. Most image sensor arrays are equipped with Bayer colour filter arrays (RGB or CMY) which means that no transparent elements (T) are usually found in the mosaic integrated with the image sensor. In FIG. 4a, the T-elements of the RGBT colour mosaic are replaced by G-elements. In case, the image sensor arrays are equipped with a CMY Bayer colour filter array, the T-elements of the CMYT colour mosaic are replaced by Y-elements, which can be illustrated by exchanging the colours R, G and B by M, Y and C, respectively, in FIG. 4, then replacing T by Y in the now resulting (sensor element wise) CMYT colour mosaic, to finally obtain a CMY colour mosaic.

Figures 6, 7:
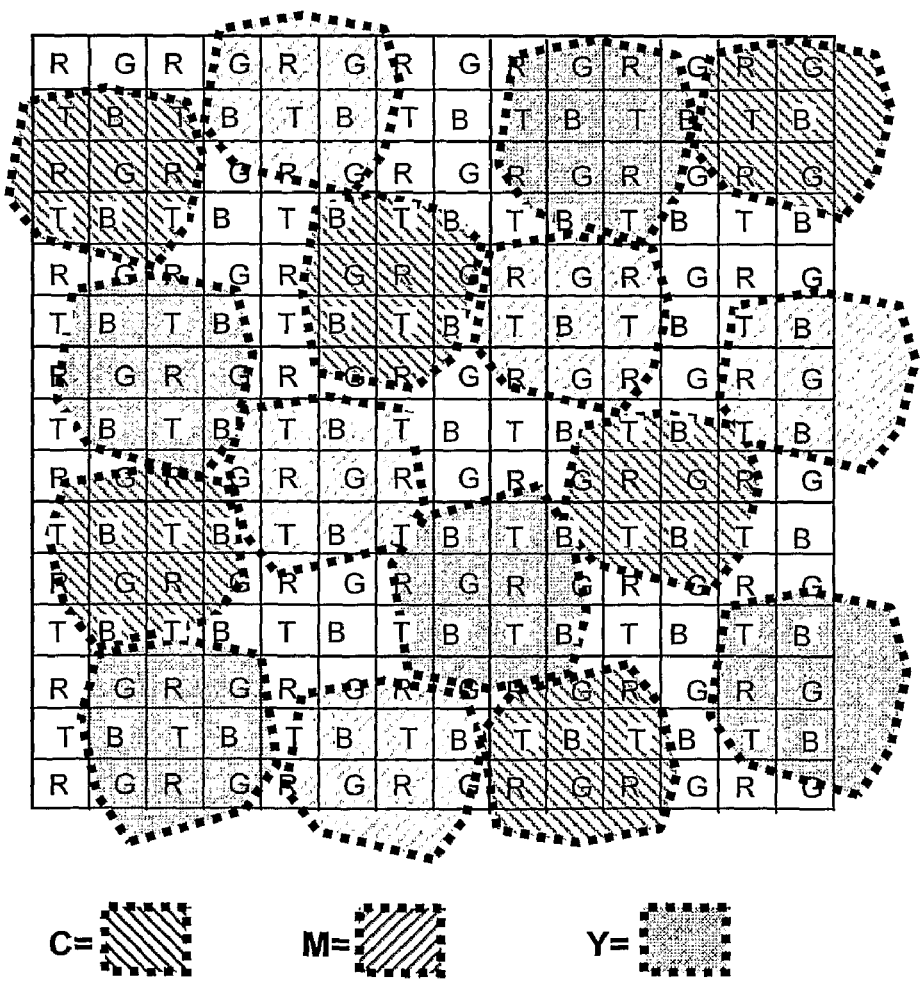

FIG. 6 illustrates the resulting multiple filter mosaic when using the colour filter mosaics in FIG. 4a. The element CR, for instance, in the multiple filter mosaic represents an area covered by both the C and R elements of the CMYT and RGBT colour mosaics, respectively.

In this description, the difference between a colour filter mosaic and a colour filter array is that the latter assumes that the sensor elements, of the image sensor, are arranged as a two dimensional array, while a colour filter mosaic doesn't have restrictions regarding the shape or the distribution of the colour filter elements, so that even randomly shaped and/or randomly distributed colour filter elements can be used. The advantage of this property of the colour filter mosaics is that higher spatial resolution can be achieved using common printing techniques even if they fail in producing a perfect or correct colour filter array with high resolution. In other words, a colour filter array is a special case of a colour filter mosaic.

FIG. 7 illustrates the case where element-wise matching is assumed being possible between the image sensor array and an RGBT colour filter array, while a lower-resolution CMYT colour mosaic with randomly distributed random-shape colour elements is overlapping the RGBT array.

Figure 8:
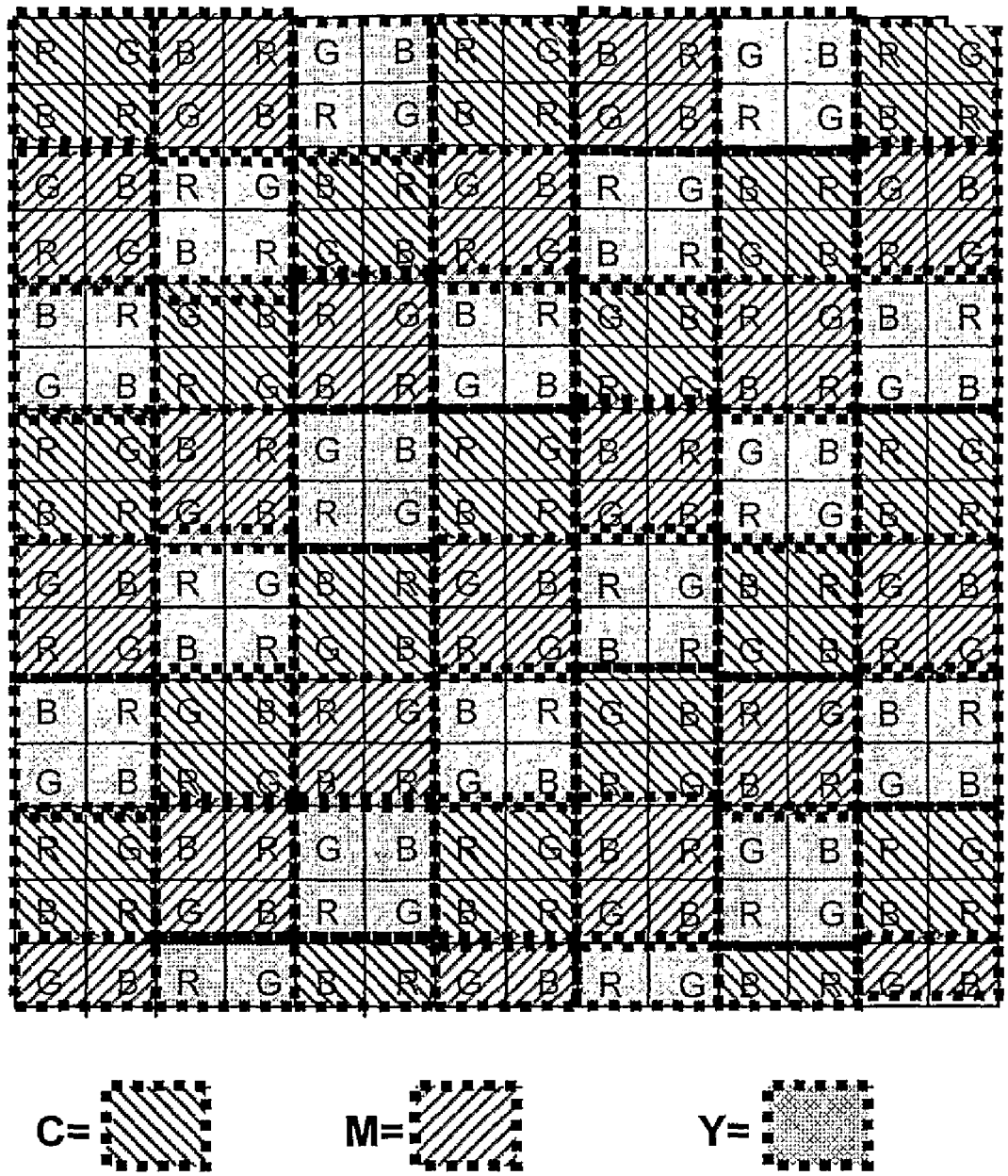
FIG. 8 is a schematic and simplified illustration of a multiple filter mosaic comprising two overlapping CMY and RGB diagonal colour mosaics, where element-wise matching is achieved between the image sensor array and the RGB mosaic, and each element of the CMY mosaic covers 2×2 elements of the RGB mosaic.

Another preferred embodiment for instantaneous imaging would use overlapping CMY and RGB diagonal colour mosaics according to FIG. 8, where element-wise matching is achieved between the image sensor array and the RGB colour mosaic (each colour area covers exactly one sensor element). Each element of the CMY colour mosaic covers exactly 2×2 elements of the RGB colour mosaic. To be able to eliminate artefacts in the registered image, diagonal colour mosaics are used so that if the C, M and Y elements are arranged on diagonals going from the upper-right corner to the down-left corner, then the R, G and B elements must be arranged on diagonals going from the upper-left corner to the down-right corner.

Figure 9:
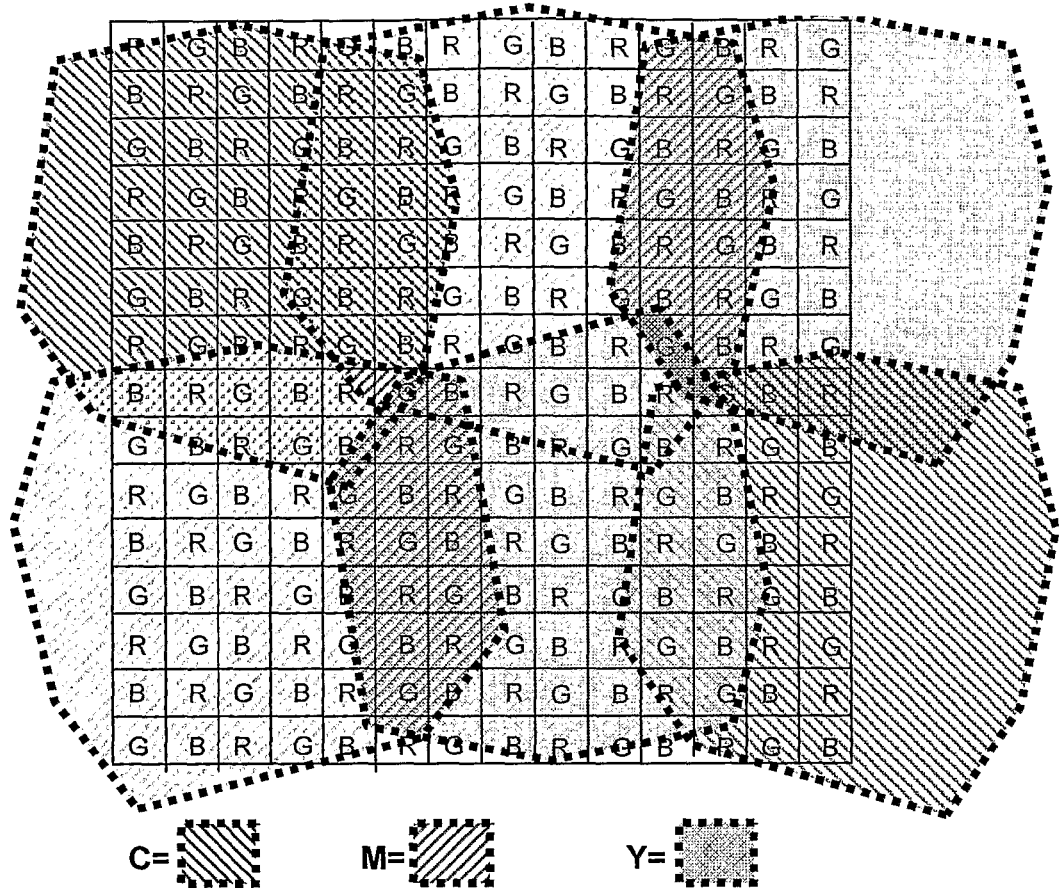
FIG. 9 is a schematic and simplified illustration of a multiple filter mosaic, where the RGB diagonal colour mosaic is integrated with the image sensor array, while the CMY diagonal colour mosaic could not be perfectly produced to contain well-separated C, M and Y areas.

FIG. 9 shows the case where the RGB diagonal colour mosaic is integrated with the image sensor array, while the CMY diagonal colour mosaic could not be perfectly produced to contain well-separated C, M and Y areas. The overlap areas, between the C, M and Y areas, also enrich the spectral content of the registered image. Each element of the CMY mosaic (can be a C, M or Y area, or any overlap area between them) must cover at least one colour element of each of the R, G and B elements of the integrated RGB mosaic.

Figure 10:
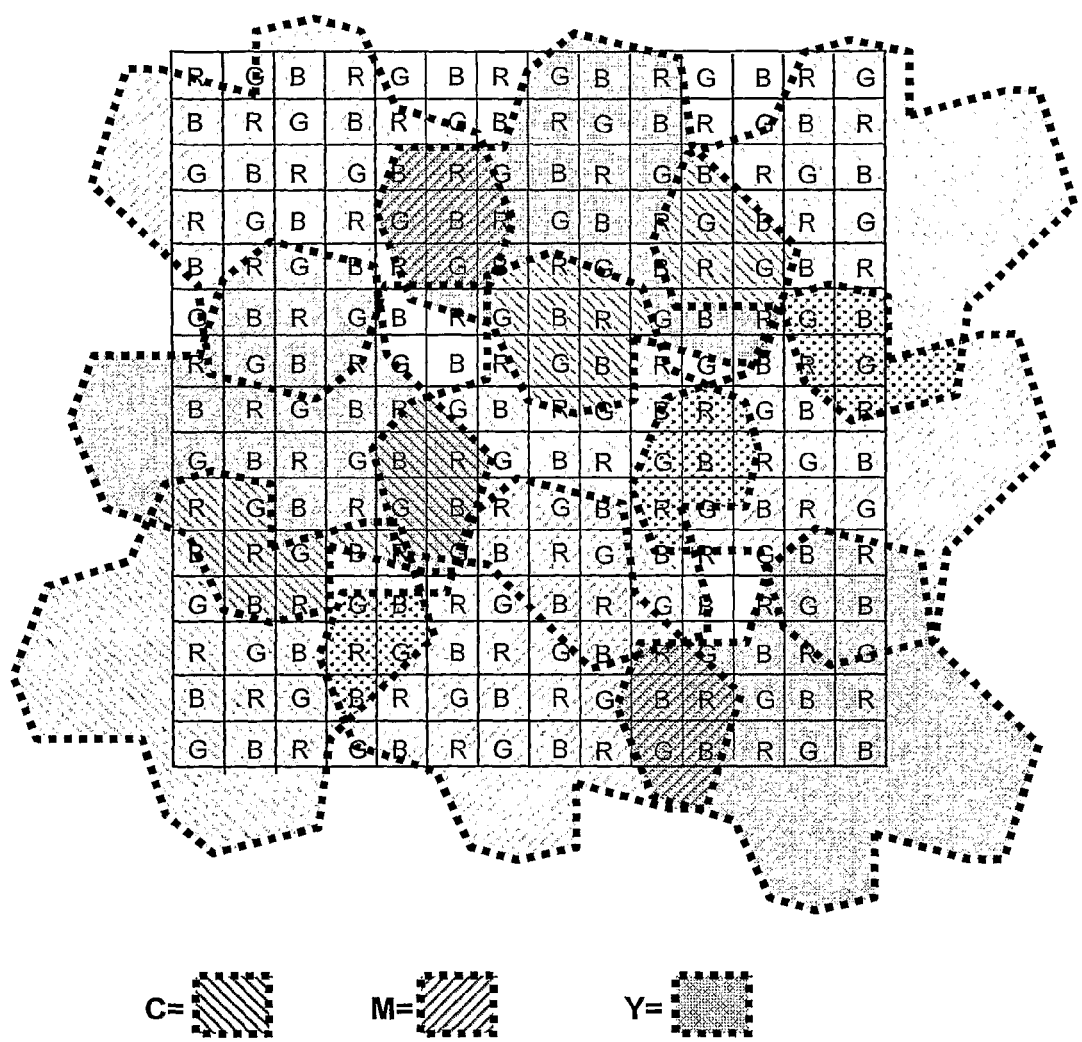
FIG. 10 is a schematic and simplified illustration of another variant of the multiple filter mosaic shown in FIG. 9, where the C, M and Y areas are diamond shaped, to prevent overlap between more than two areas of the CMY mosaic.

FIG. 10 shows another variant of the case in FIG. 9, where the C, M and Y areas are diamond shaped, to prevent overlap between more than two areas of the CMY mosaic.

Figure 11:
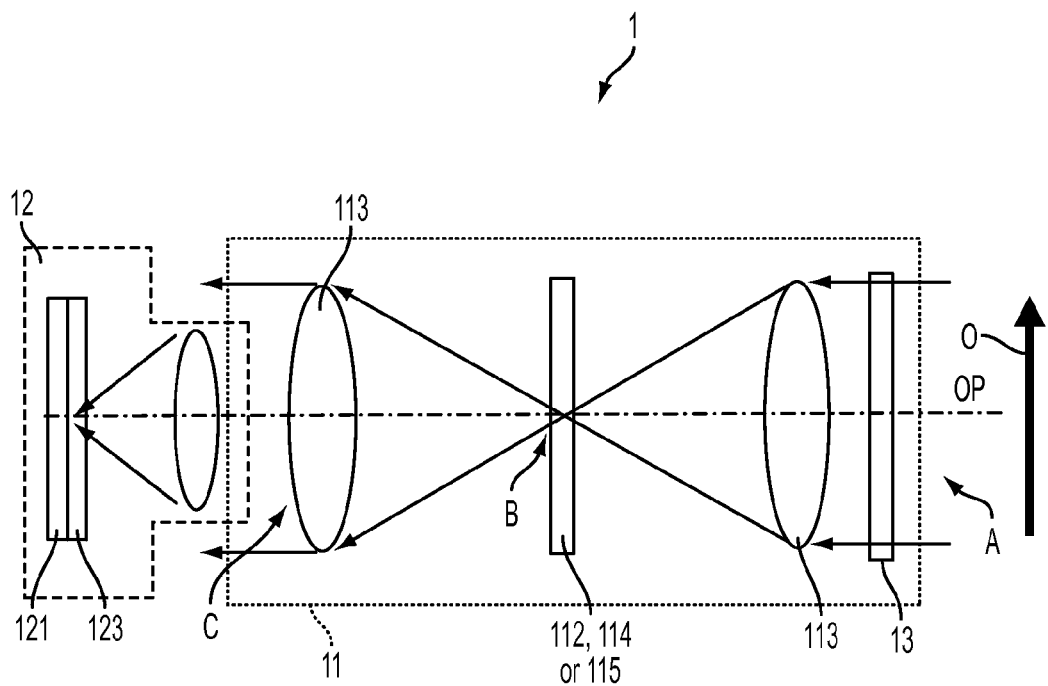
FIG. 11 is a schematic and simplified illustration of an embodiment of the invention where a single-chip image sensor (comprising one sensor array) is used. The arrangement 1 (which comprises first uniform spectral filters 13) can be attached to a conventional digital camera that is equivalent to part 12 in the figure.

With reference to FIG. 11 an arrangement 1 for the production of instantaneous or non-instantaneous multi-band images, to be transformed into multi- or hyperspectral images, will now be described.

The arrangement 1 comprises light collecting means 11, an image sensor 12 with at least one two dimensional sensor array 121, and an instantaneous colour separating means 123, positioned before the image sensor array 121 in the optical path OP of the arrangement 1.

The arrangement 1 also comprises first uniform spectral filters 13 in the optical path OP, with the purpose of restricting imaging to certain parts of the electromagnetic spectrum.

In the case of instantaneous imaging, the present invention specifically teaches that at least one first spectral or colour filter mosaic 112 is either permanently or interchangeably positioned before the colour separating means 123 in the optical path OP in, or at least as close as possible to, converged light B. The first spectral or colour filter mosaic 112 being interchangeably positioned gives a possibility to easily switch between different first spectral or colour filter mosaics 112 (i.e. filter exchange) in order to adapt the arrangement 1 to different optical requirements and hence to different spectral measurements. It is, of course, also possible to permanently place the first spectral or colour filter mosaic 112 before the colour separating means 123 in the optical path OP in, or at least as close as possible to, converged light B.

The light collecting means 11 also comprises any lenses 113 and/or mirrors required to focus incoming light A into converged light B, and thereafter into outgoing approximately collimated light C. The lens system thereby optically moves incoming light from an object O, to approximate infinity. The lens system should be able to accommodate to objects at various distances. These optical components are however not described in detail since the present invention does not relate to this optical part of the arrangement, since these optical parts may be realised in many different ways, and since they are obvious for the skilled person. For the same reason are image processing units and some other hardware/software parts needed for spectral calculations not described in detail in the description or depicted in the figures.

The first spectral or colour filter mosaic 112 consists of a multitude of small homogeneous filter regions (or filter elements) arranged as a repetitive pattern, and the transmission curves (TC, which is defined as the filter transmission as a function of the wavelength) of these colour regions of the first spectral or colour filter mosaic 112 are partly overlapping, in addition to overlap between these transmission curves and those belonging to the filter elements of the colour separating means 123. The transmission curves TC of the first spectral or colour filter mosaic 112 and those of the colour separating means 123 must be spread out in the wavelength interval(s), of the spectrum, to be considered or studied.

In the case of non-instantaneous imaging, the present invention teaches that at least one colour filter wheel 114 (instead of a filter mosaic 112) is positioned before the colour separating means 123 in the optical path OP in, or at least as close as possible to, converged light B. Uniform colour filter interchange is performed, by utilising the filter wheel, to spectrally scan the whole image cube, yielding a non-instantaneous image. The same considerations, as in the case of using a filter mosaic 112, must be taken into account, regarding the transmission curves TC of the filters mounted on the filter wheel 114 and those of the colour separating means 123 and the relationship between them.

A more general approach, is to place at least one flat thin transmissive display 115 (instead of a filter mosaic 112 or a filter wheel 114) before the colour separating means 123 in the optical path OP in, or at least as close as possible to, converged light B. Instantaneous imaging is achieved if the display 115 is used to generate a colour filter mosaic, while interchanging a series of uniform colour filters (i.e. generating them in succession) yields non-instantaneous images. The same considerations, as in the case of using a filter mosaic 112 or a filter wheel 114, must be taken into account, regarding the transmission curves TC of the filters displayed by the transmissive display 115 and those of the colour separating means 123 and the relationship between them.

Figure 12:
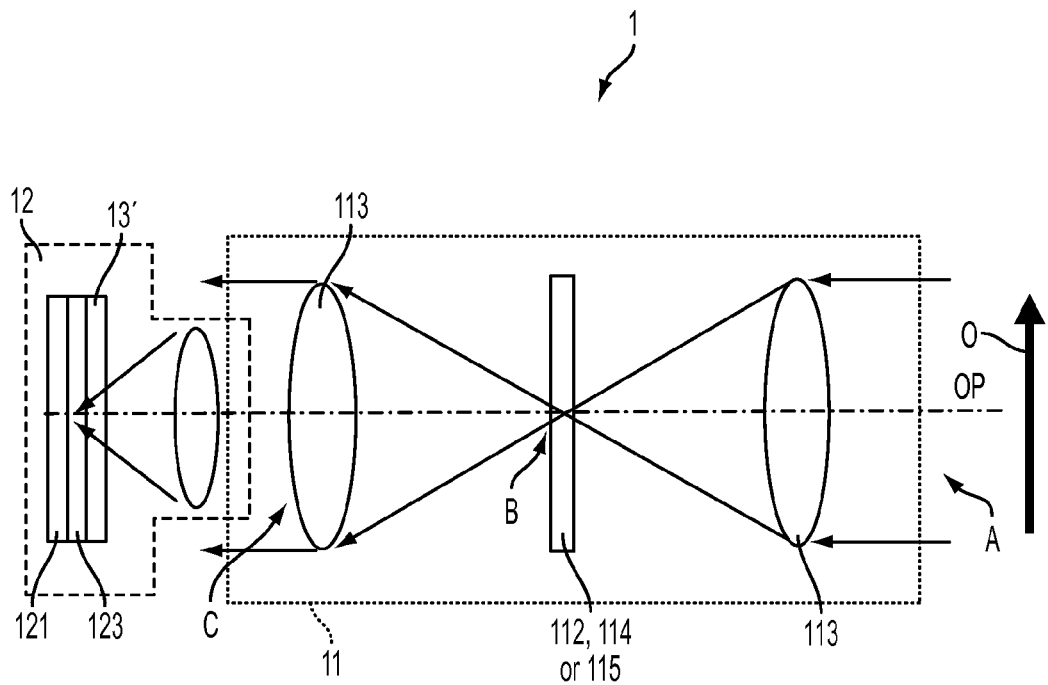
FIG. 12 is a schematic and simplified illustration of another variant of the embodiment shown in FIG. 11, where the first uniform spectral filter is a part of the used conventional camera.

A conventional camera usually comprises uniform spectral filters used to restrict imaging to certain parts of the electromagnetic spectrum. It is also proposed that these uniform spectral filters, being parts of the conventional camera, constitutes the first uniform spectral filters 13', according to FIG. 12.

Figure 13:
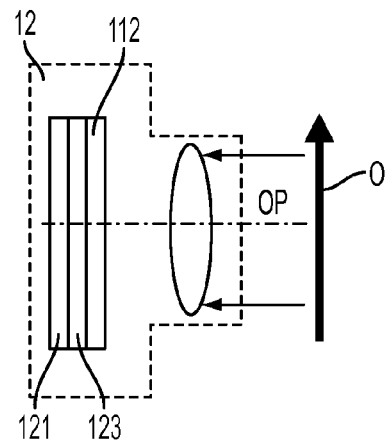
FIG. 13 is a schematic and simplified illustration of an embodiment of the invention where a single-chip image sensor is used, and the first spectral or colour filter mosaic 112 directly covers the colour separating means 123.

In another embodiment, the first colour filter mosaic 112 can be positioned to directly cover the colour separating means 123 as shown in FIG. 13. The filter mosaic 112 can either be loosely placed over the colour separating means 123, or integrated with 123. This arrangement is used for the production of instantaneous multi-band images, to be transformed into multi- or hyperspectral images.

The combination of the colour separating means 123 on one hand, and a first colour filter mosaic 112, or a series of uniform colour filters used in a filter wheel 114, or a colour filter mosaic or a series of uniform colour filters generated by a transmissive display 115, on the other hand, produces different sets of linearly independent multiple colour filter transmission curves TC.

Figure 14:
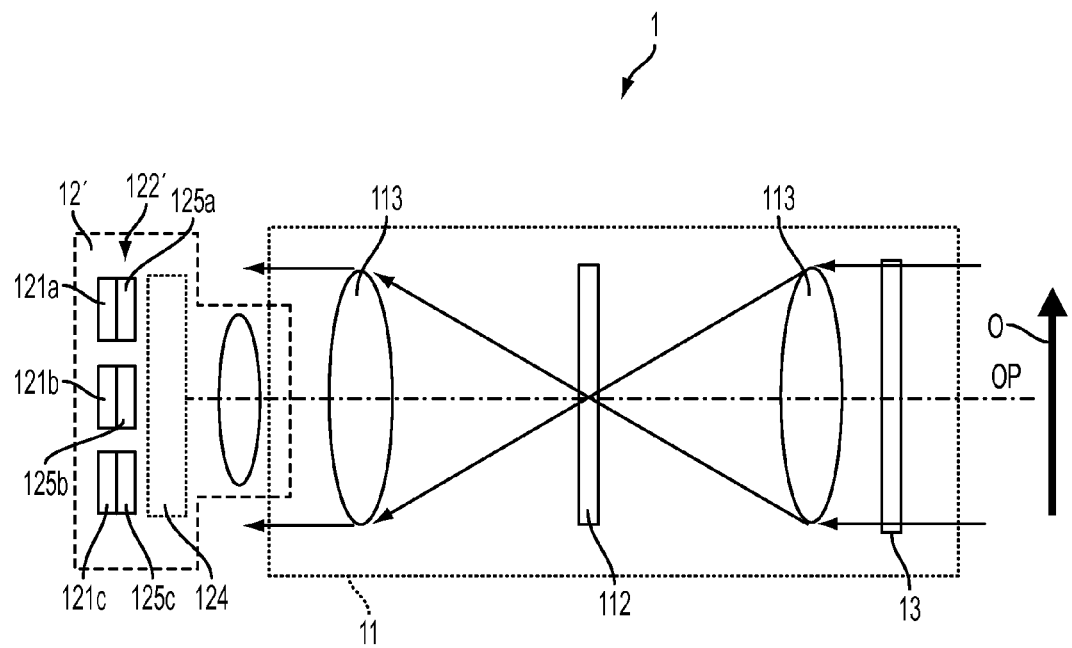
FIG. 14 is a schematic and simplified illustration of an embodiment of the invention where a 3-chip image sensor (comprising three separate sensor arrays covered by three different uniform filters) is used. The arrangement 1 can be attached to a conventional 3-chip digital camera that is equivalent to part 12' in the figure.

FIG. 14 shows the use of an image sensor 12' comprising three separate two dimensional sensor arrays 121*a*, 121*b* and 121*c*; i.e. a 3-chip camera. In this case the colour separating means 122' comprises means for separating incoming light into three different spectral or colour bands, one band to respective two dimensional sensor array, 121*a*, 121*b* or 121*c*. There are different ways of achieving this. One possible solution is the use of a beam splitter 124 in addition to three separate uniform colour filters 125*a*, 125*b* and 125*c*. It is also possible to use a colour separating beam splitter without the separate uniform colour filters, thus achieving the same optical result. The details of the embodiment in FIG. 14 are the same as the embodiment in FIG. 11 as described previously.

Figure 15:
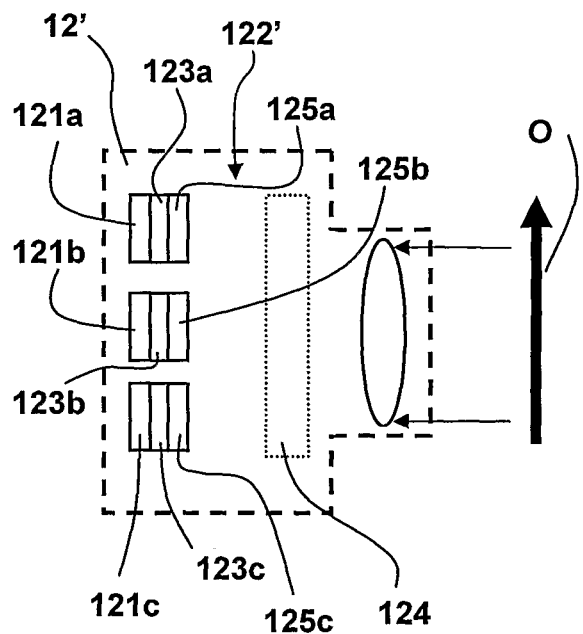
FIG. 15 is a schematic and simplified illustration of an embodiment of the invention where a 3-chip image sensor is used, and each multiple filter mosaic, comprising a uniform colour filter (125a, 125b or 125c) and a colour filter mosaic (123a, 123b or 123c), directly covers one of the separate sensor arrays.

The embodiment in FIG. 15 presents a 3-chip camera with an image sensor 12' comprising three separate two dimensional sensor arrays 121*a*, 121*b* and 121*c*. Here also, a colour separating means 122' is used comprising a beam splitter 124 in addition to three separate uniform colour filters 125*a*, 125*b* and 125*c*. In addition to that, three colour filter mosaics, 123*a*, 123*b* and 123*c*, are used to form multiple filter mosaics when combined with the uniform colour filters 125*a*, 125*b* and 125*c*. Here also, it is possible to achieve the same optical result by using a colour separating beam splitter without using the separate uniform colour filters, i.e. the uniform colour filters 125*a*, 125*b* and 125*c*, are omitted from FIG. 15. The colour filter mosaics, 123*a*, 123*b* and 123*c*, can have identical or different colour filter patterns.

Figure 16:
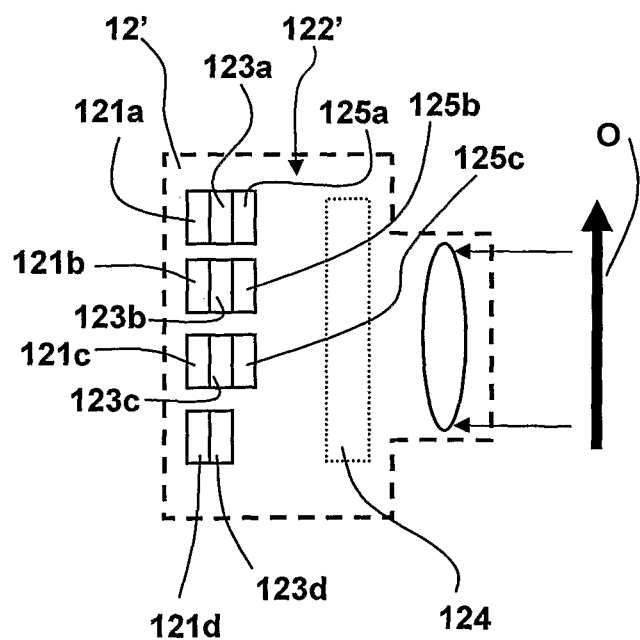
FIG. 16 is a schematic and simplified illustration of an embodiment of the invention where a 4-chip image sensor is used, and different multiple filter mosaics directly cover different separate sensor arrays.

The embodiment in FIG. 16 presents a 4-chip camera with an image sensor 12' comprising four separate two dimensional sensor arrays 121*a*, 121*b*, 121*c* and 121*d*. All details are the same as for the embodiment in FIG. 15 except that the fourth image sensor array 121*d* doesn't use any uniform colour filter after the beam splitter, i.e. in the case of using a colour separating beam splitter, it must provide a signal comprising the whole spectrum to the fourth image sensor array 121*d*. A colour filter mosaics 123*d* (that can have identical or different colour filter pattern as 123*a*, 123*b* and 123*c*) is used for the fourth image sensor array 121*d*.

For the embodiments presented in the FIGS. 11, 12, 13, 14, 15 and 16, the preferred multiple colour filter mosaics are illustrated by FIGS. 4*a* and 5, as well as FIGS. 7, 8, 9 and 10 where practical aspects are taken into account. The case, where the spatial resolution of the CMYT colour mosaic is higher than the spatial resolution of the RGBT colour mosaic, is also considered. This is achieved by exchanging the colours R, G and B by M, Y and C, respectively, in FIGS. 4*a* and 5. It is of course preferred to achieve element-wise matching between the image sensor array and the higher resolution colour filter mosaic, and to let each element from the lower resolution mosaic to cover exactly 2×2 elements of the higher resolution mosaic. It is also possible to equip the image sensor array with an RGB Bayer colour filter array, where the T-elements of the RGBT colour mosaic are replaced by G-elements in FIGS. 4*a* and 5. In case, the image sensor array is equipped with a CMY Bayer colour filter array, the T-elements of the CMYT colour mosaic are replaced by Y-elements, which can be illustrated by exchanging the colours R, G and B by M, Y and C, respectively, in the FIGS. 4*a*, 5, 7, 8, 9, and 10. In the case of FIGS. 4*a* and 7, the T-elements are replaced by Y in the resulting (sensor element wise) CMYT colour mosaic, to finally obtain a CMY colour mosaic with the same resolution as the image sensor array.

A preferred embodiment of the present invention proposes that a conventional digital camera is a part of the inventive arrangement, where the image sensor 12, 12' and colour separating means 123, 122' (as illustrated in FIGS. 11, 12, 13, 14, 15 and 16) are parts of the conventional camera.

The transmission curves of the colour filters or colour mosaic elements can easily be measured by standard spectroradiometers (also called spectrometers). This is not the case when the uniform colour filter or the colour mosaic is integrated with the sensor, where it is possible to measure these transmission curves by taking an image of a whole rainbow and looking at a line of pixels going through all colours in this picture. These pixel values represent the transmission curve of the used uniform colour filter. In the case of an RGB colour mosaic, one can take the R, G, and B bands of the resulting colour picture to represent estimates of the transmission curves of the R, G, and B colour filter elements of the used mosaic. These curves are graded by using a spectroradiometer to measure and estimate the wavelengths at different points along the chosen line across the rainbow image. It is also possible to measure or estimate the transmission curves of other colour mosaics in analogous ways. These measurements are input to the transformation of the inventive method, i.e., how to convert the measured bands into discrete spectra, which will be discussed in more detail below. Hence, when using the inventive arrangement, the use of auxiliary apparatus such as for instance spectroradiometers or rainbow projectors, is presupposed if the spectral properties of the colour mosaics are not fully known.

Figure 17:
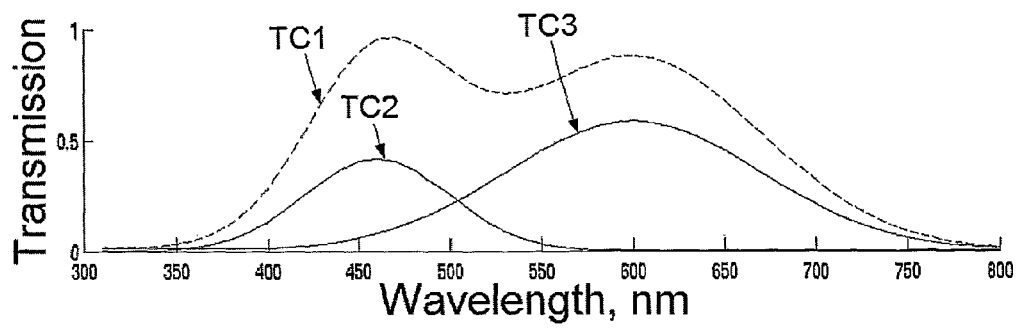
FIG. 17 is a schematic and simplified illustration of linearly dependent transmission curves of filters, where the transmission curve TC1 is a linear combination of the two other transmission curves TC2 and TC3.
Figure 18:
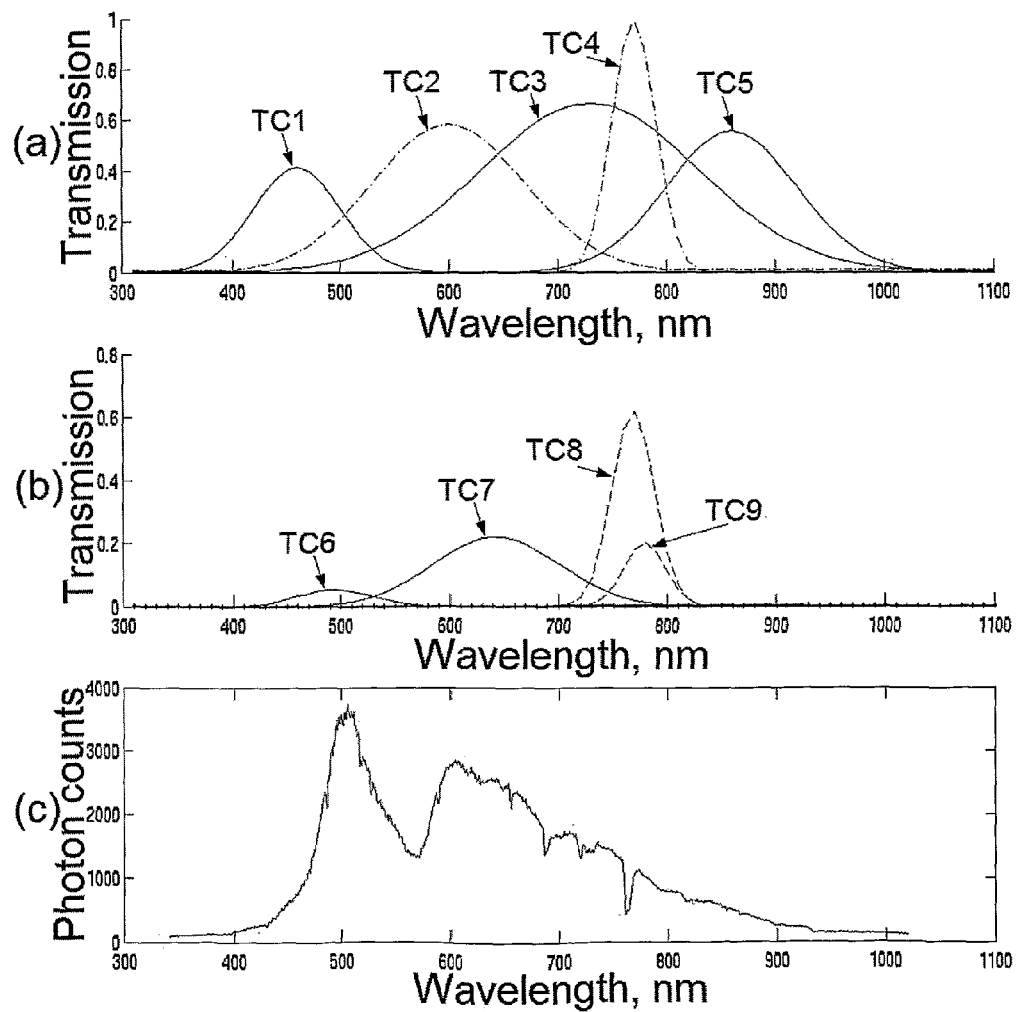
FIG. 18a shows five filter transmission curves, TC1, TC2, TC3, TC4 and TC5.
FIG. 18b shows the transmission curves, TC6, TC7, TC8 and TC9, which are the results of multiplying pairs of the transmission curves from FIG. 18a, TC1 by TC2, TC2 by TC3, TC3 by TC4, and TC4 by TC5, respectively.
FIG. 18c shows a real spectrum, of a colour filter, registered by a conventional spectrometer.

Multiple colour filters with linearly independent transmission curves TC (fraction of light transmitted as a function of wavelength) are generated by combining different colour filters that can be uniform colour filters and/or small elements in colour filter mosaics generated by different means, such as transmissive displays as well as printing and photographic printing techniques. The term linear independent is defined in any mathematical handbook, and simply means that each transmission curve cannot be obtained by multiplying another transmission curve by a constant, or by a linear combination of other transmission curves. An example of linear dependence is illustrated by FIG. 17, where the dashed transmission curve TC1 is a linear combination of the two other solid transmission curves TC2 and TC3. Transmission curves, of colour filters produced by common printing techniques, consist typically of two flattish regions and a steeply sloping portion of the transmission curve in between, which is a good property, when forming multiple colour filters. Two narrow peaks (e.g. for a magenta colour filter) is another useful printed filter element that can be achieved using these techniques. The transmission curve of a multiple colour filter is approximately the result of element-wise multiplication of the transmission-curve vectors of the constituent colour filters that form this multiple filter. As an illustrating example, five transmission curves, TC1, TC2, TC3, TC4 and TC5, are presented in FIG. 18*a*, and the results of some element-wise multiplication between pairs of them are presented in FIG. 18*b* where TC6, TC7, TC8 and TC9, are the results of multiplying, TC1 by TC2, TC2 by TC3, TC3 by TC4, and TC4 by TC5, respectively. FIG. 18*c* shows a real spectrum, of a colour filter, registered by a conventional spectroradiometer.

A colour filter mosaic that is integrated or embedded in the image sensor cannot easily be detached. The important implication is that this prevents a user from flexibility in changing mosaic for his application and precludes the use of traditional printing techniques for producing cheap colour mosaics. Furthermore, the user can not easily measure optical properties of embedded colour filter mosaics. The present invention teaches that it is always possible to use non-integrated colour filter mosaics consisting of low-cost broadband filter elements or low-cost dichroic filters. But in case it is demanded by the application, expensive narrow band filters or mosaics consisting of such filters can be of course used.

With the purpose of providing a cost effective way of implementing the present invention, it is proposed that the colour filter mosaics can be produced by existing colour (laser or ink) printing techniques or by other current photographic printing techniques, on transparent materials.

The basic idea of the present invention is to attempt to circumvent the use of expensive narrow band filters (uniform filters or filter mosaics) by exploiting combinations of low-cost broadband filters or low-cost dichroic filters. One such type of low-cost filters or mosaics is, in fact, printed patterns on transparent material e.g. transparency film. It is possible to use a traditional colour laser printer, to produce colour mosaics of resolution down to 200 elements per inch. Another philosophy behind the present invention is to make use of the currently available mass-produced colour filters, by using both a printed colour mosaic in the optical path, and the colour mosaic integrated with the image sensor. The camera manufacturers have developed quality colour mosaics (e.g., CMYG, CMY, RGB, RGBE, etc.) and the industries dealing with printing techniques have developed high quality colour print (often CMYK, where K=black). Both these two branches of industry have a long development history in the quest of attaining in some sense optimal filters, and there is a parallel trend towards increasing quality as well as increasing spatial resolution, and reducing the cost, which implicitly works in favour of the present invention.

Converged light means a positions in space towards which bundles of rays of light tend to converge. The convergence is never exact due to the nature of light and imperfections in the optical systems, but in common day speech, these regions are usually referred to as intermediate images. Colour filter mosaics printed on ordinary transparency film is far from being transparent, and seemingly useless for colour filters, but when they are placed in converged light they attain almost perfect transparency. Being far away from converged light has the blurring side effects.

Figure 19:
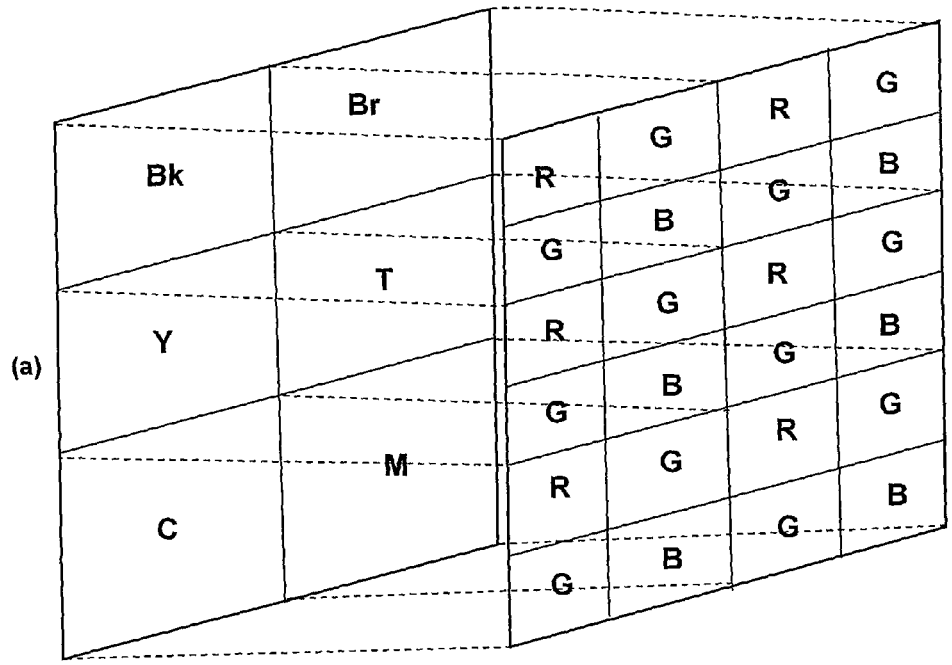
FIGS. 19a and 19b are schematic and simplified illustrations of two multiple filter mosaics suitable for agricultural and medical applications.
Figure 19:
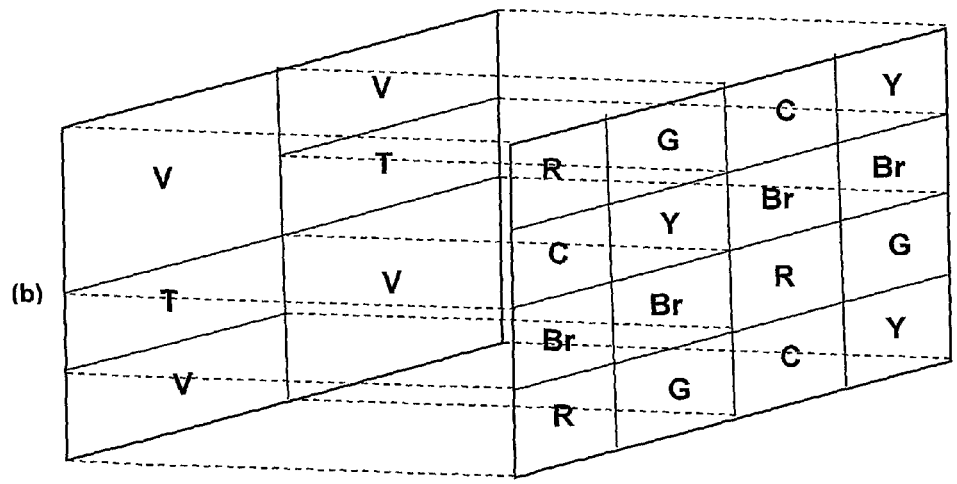

FIG. 19a illustrates an embodiment suitable for agricultural and medical applications of multi- and hyperspectral measurements. Here it is crucial to include band(s) in the near infrared region of the spectrum. In that case, a simple mosaic design is to use a CMYTBrBk mosaic (Br=brown, Bk=black) in the first colour filter mosaic 112, in conjunction with the colour separating means 123 (an RGB colour filter mosaic), which is embedded or integrated with the image sensor. The black and brown mosaic elements are selective for bands in the near infrared portion of the spectrum. The infrared blocking filter included in most image sensors must then be removed. This produces some desirable multiple filters. The colour filter elements are obtained from simple printing procedures, for example on a colour printer on transparent material.

FIG. 19b illustrates another colour filter mosaic embodiment, showing that a pattern consisting of 6 filter elements could be used in the first colour filter mosaic 112 in addition to a second adjacent layer with a VT mosaic, where V stands for visible portion of the electromagnetic spectrum (V=infrared blocking, T=transparent in the visible and near infrared spectral regions). The image sensor is, in this special case, monochrome without infrared blocking filter.

Figure 20:
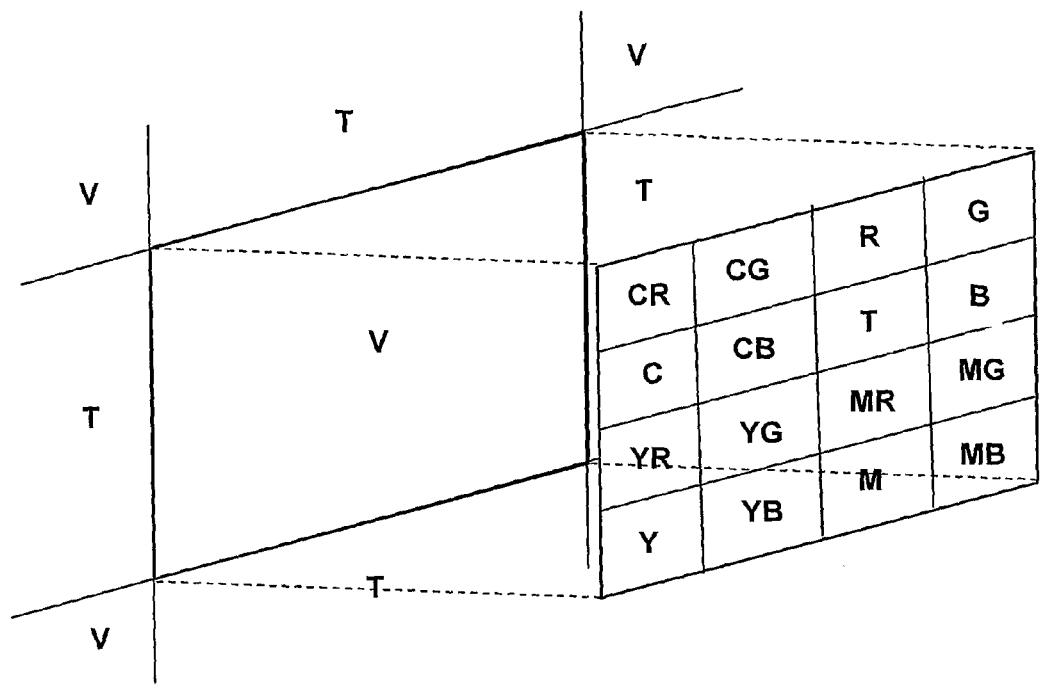
FIG. 20 shows a schematic and simplified illustration of a multiple filter mosaic suitable for medical and agricultural applications.

FIG. 20 illustrates an embodiment suitable for medical and agricultural applications of multi- and hyperspectral measurements. Here, the multiple filter mosaic illustrated in FIG. 6 is combined with a VT mosaic. The image sensor is, in this special case, monochrome without infrared blocking filter. It is, of course, also possible to use an image sensor equipped with an RGBT mosaic and add a multiple filter mosaic built of a CMYT mosaic and a VT mosaic, as illustrated in FIG. 4a and FIG. 20, respectively. Another possibility is to use an image sensor equipped with an RGB mosaic (as described earlier where the T-elements of the RGBT colour mosaic were replaced by G-elements) and add a multiple filter mosaic built of a CMYT mosaic and a VT mosaic.

In general, the current trend of having million pixel images in digital cameras implies that the loss of resolution for using pattern of 4-, 9- or 16-elements in the mosaics may be tolerable. Note, however, that we generally speaking attempt to increase the spectral information by using multiple filters.

Layered photodiode sensing, where a single sensor is able to simultaneously capture three broad R, G and B spectral bands, is presented in the publication "Real-time color imaging with a CMOS sensor having stacked photodiodes" by David L. Gilblom, Sang Keun Yoo and Peter Ventura, in Proceedings SPIE, Volume 5210, pp. 105-115 (2004). These sensors are also called triple-well image sensors, since each CMOS sensor element contains three p-n junctions at various depths. This special single-chip image sensor is equivalent to using a three-chip image sensor equipped with R, G and B uniform colour filters, each of which covering one of the three sensor-chips. Adding a CMYT mosaic to this sensor array will produce a multiple filtering effect similar to the cases presented previously in the text and figures. To achieve the best possible spatial image-resolution, pixel wise matching is preferred between the CMYT mosaic elements and the triple-layered image-sensor-array elements, i.e. the CMYT mosaic is integrated with the image sensor chip. However, the CMYT mosaic can be placed in any position in the optical path (OP) where converged light is found, as described previously in the text and figures.

However, it is also possible to construct layered photodiodes with more than three layers that include near ultraviolet and/or near infrared sensitive layers. Covering the layered-sensor-element array with a proper colour filter mosaic, such as CMYT or CMYTBk, produces useful spectral light-signal responses that is spectrally rich enough to be converted into spectra covering the near-ultraviolet, visible as well as the near-infrared wavelength regions.

Figure 21:
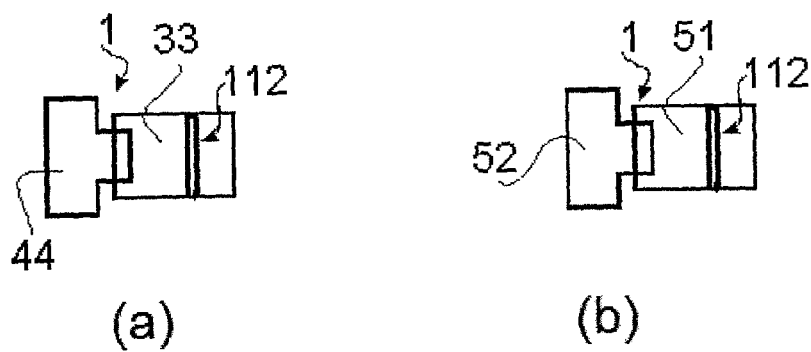
FIG. 21a shows an optical auxiliary device 33 that comprises at least one first spectral or colour filter mosaic 112 according to the present invention. The inventive optical device 33 and the conventional camera 44 form an inventive arrangement 1 when connected to each other.
FIG. 21b shows an ocular 51 that comprises at least one first spectral or colour filter mosaic 112 according to the present invention. The ocular 51 in co-action with a conventional digital camera 52 form an inventive arrangement 1.

FIG. 21a shows an optical auxiliary device 33 that comprises at least one first colour filter mosaic 112 according to the present invention. The optical device 33 is adapted to be connected to a conventional digital camera 44 in a manner to align the optical axis of the optical device 33 with the optical axis of the camera 44. The camera doesn't have an own camera lens, and the optical device 33 functions as a camera lens equipped with colour filter mosaics. The inventive optical device 33 and the conventional camera 44 form an inventive arrangement 1 when connected to each other.

FIG. 21b shows an ocular 51 that comprises at least one first colour filter mosaic 112 according to the present invention. The ocular 51 in co-action with a conventional digital camera 52 (the camera has its own camera lens) form an inventive arrangement 1. It is important to align the optical axis of the ocular 51 with the optical axis of the camera 52. The colour filter mosaic 112 may be adapted to an insertion into a conventional ocular 51 embedded into, for instance, a telescope, a binocular or a microscope. The colour filter mosaic 112 should be disposed close to an intermediate image in the optical path. This should be done inside the light collecting means 11 in previously shown embodiments (in FIGS. 11, 12 and 14) or in the ocular 51 in the latter embodiment (in FIG. 21b). Most lens systems of microscopes, telescopes and binoculars have ocular parts suitable for mechanical insertion of colour filter mosaic plates. For a more detailed discussion, see publication WO 00/41010.

The orientation and dimensions of colour mosaics may in a simple embodiment be free, but it is desirable to achieve pixel-wise matching between the a colour mosaic and the image sensor array, and to achieve element-wise matching between a colour mosaic and another one with elements that cover exactly 2×2, 2×3, 3×3 or other number of elements of the first one (the higher resolution mosaic), i.e. the two colour mosaics are exactly matched. The image processing software (can be built-in inside the camera box, or installed on a computer to which the images are transferred from the camera) automatically finds the regions affected by the different colour mosaic elements in the image by using a simple calibration procedure. Taking images of white background or white light may for instance calibrate the imaging system and help in identifying and segmenting the different colour mosaic element areas in the image. It is assumed that the colour mosaics doesn't change place nor orientation afterwards to be able to assume that the same multiple filter mosaic or pattern is still valid when taking new images of arbitrary scenes. In other words, exactly the same segmentation (of the white-background image) is performed on the new images. Whenever a colour mosaic (which is used in the multiple filter unit MFU in FIG. 1) is changed or the place or orientation of a colour mosaic are changed, a new white-background image must be registered to be used to calibrate the images registered using the current colour mosaics.

The image registered by the image sensor unit (ISU) using a multiple filter unit (MFU) that comprises colour filter mosaics, as illustrated by the figures starting with FIG. 1, will consist of small neighbouring regions each of which is affected by a certain mosaic-filter element, i.e. the sensor elements that registered this region of the image is covered by that mosaic-filter element. A white background colour-normalised image can be used to be able to identify image pixels that belong to a specific mosaic-filter element, and the gained information is used to extract the corresponding pixels (that have exactly the same coordinates as the chosen white-background image pixels) from arbitrary images and put them in a separate array (which has the same size as the image) which will consequently contain empty elements. These separate arrays are as many as the different mosaic-filter elements that can be found in the multiple filter unit (MFU). The arrangement in FIG. 4a will for instance produce 16 partly filled (porous) arrays, where only one array-element is filled when considering all array-elements with the same coordinates in all arrays. This means that each pixel from the registered image will belong to only one of these separate arrays. This task can be seen as a kind of demosaicking procedure.

The remaining empty array-elements can be filled using a sort of interpolation procedure. The following two approaches are preferred.

Interpolation Using Distance Transform

Figure 22:
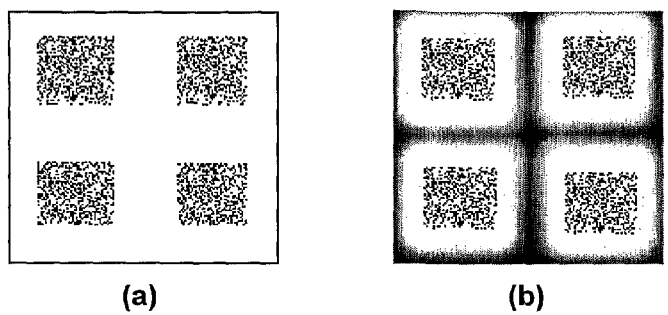
FIG. 22a shows a portion of a separate 2D-array, where the shaded areas represent homogeneous areas.
FIG. 22b shows the result of applying the distance transform to the portion of the separate array in FIG. 22a, where darker elements correspond to larger distances.

FIG. 22a shows a portion of a separate array, generated by the demosaicking procedure mentioned above, where the shaded or dotted areas (representing homogeneous areas) represent regions belonging to the same element of the used multiple filter mosaic. The goal here is to fill in the empty elements in the array (i.e. the white areas in FIG. 22a).

The distance transform can be used to calculate the distance between each empty element and the nearest shaded element. FIG. 22b shows the result of applying the distance transform to the portion of the separate array in FIG. 22a, where darker elements correspond to larger distances. For every separate array (the whole array), the interpolation (can also be seen as extrapolation) begins with the white elements and ends with the black ones.

It is also possible to use kriging to fill-in the empty spaces of an array.

Interpolation Using Statistical Transformation

In this approach each multiple filter response is transformed into the corresponding responses of other multiple filters. In the case presented by FIG. 4a, it is necessary to estimate the required coefficients to be able to transform the responses each of the multiple filters, presented in FIG. 6, into all other ones' responses. The transformation coefficients can be calculated using a linear system of equations as follows:

$$F_i C_{ij} = F_j \quad (\text{Eq. 1})$$

Where $F_i$ and $F_j$ are two matrices consisting of the responses of the groups of multiple filters i and j, respectively, and $C_{ij}$ contains the transformation coefficients for transforming $F_i$ into $F_j$. The solution of a system of linear equations of the form Ax=y (where the matrix A and the column vector y are known, while the column vector x is unknown) is $x = A^T (AA^T)^{-1} y$, where $A^T(AA^T)^{-1}$ is the pseudo inverse of A (where $A^T$ denotes the transpose of matrix A, and $A^{-1}$ denotes the inverse of matrix A). Analogously, the coefficient matrix $C_{ij}$ can be estimated as follows:

$$C_{ij} = F_i^T (F_i F_i^T)^{-1} F_j \quad (\text{Eq. 2})$$

As an illustrating example, lets look at the case of transforming the responses of the multiple filters CR, CG, CB and C, into the responses of MR, MG, MB and M. Here we have the following system of equations:

$$F_C C_{CM} = F_M \quad (\text{Eq. 3})$$

Where the matrices $F_C$ and $F_M$ consist of N (where N is an integer number) rows and four columns, while $C_{CM}$ is a 4×4 matrix, as follows:

$$F_C = \begin{bmatrix} CR & CG & CB & C \\ x & x & x & x \\ x & x & x & x \\ \dots & \dots & \dots & \dots \\ \dots & \dots & \dots & \dots \\ x & x & x & x \end{bmatrix} \quad F_M = \begin{bmatrix} MR & MG & MB & M \\ x & x & x & x \\ x & x & x & x \\ \dots & \dots & \dots & \dots \\ \dots & \dots & \dots & \dots \\ x & x & x & X \end{bmatrix}$$

$$C_{CM} = \begin{bmatrix} x & x & x & x \\ x & x & x & x \\ x & x & x & x \\ x & x & X & x \end{bmatrix}$$

Where the four columns of $F_C$ contains the responses of the multiple filters CR, CG, CB and C, while the columns of $F_M$ contains the responses of MR, MG, MB and M, to exactly the same light signals and presented on the rows of the matrices in exactly the same order; e.g. the values on the first rows of both of $F_C$ and $F_M$ correspond to the responses of the multiple filters CR, CG, CB and C, as well as MR, MG, MB and M, to exactly the same light signal. The coefficient matrix $C_{CM}$ is estimated by using equation (Eq. 2) yielding:

$$C_{CM} = F_C^T (F_C F_C^T)^{-1} F_M \quad (\text{Eq. 4})$$

The estimated transformation matrix $C_{CM}$ is then used to transform new measured responses of the multiple filters CR, CG, CB and C, into the corresponding responses of MR, MG, MB and M. The values used in $F_C$ and $F_M$ to estimate $C_{CM}$ are belong to a so-called training data set.

The same method can be applied to estimate the other needed transformation matrices to be able to fill-in and complete the separated or demosaicked (porous) arrays (e.g. 16 such arrays must be processed in the case of using the multiple filter mosaic presented in FIG. 4a). Note that the inverse transformations are also needed, e.g. $C_{MC}$ for transforming $F_M$ into $F_C$. However, the same training data set, that was used to estimate $C_{CM}$, can be used to estimate $C_{MC}$ as follows: $C_{MC} = F_M^T (F_M F_M^T)^{-1} F_C$.

As another illustrating example, lets look at the case presented in FIG. 8. Here, no transparent filter elements are used in the colour mosaics, yielding for instance the following $F_C$, $F_M$ and $C_{CM}$ matrices:

$$F_C = \begin{bmatrix} CR & CG & CB \\ x & x & x \\ x & x & x \\ \cdots & \cdots & \cdots \\ \cdots & \cdots & \cdots \\ x & x & x \end{bmatrix} \quad F_M = \begin{bmatrix} MR & MG & MB \\ X & x & x \\ X & x & X \\ \cdots & \cdots & \cdots \\ \cdots & \cdots & \cdots \\ X & x & X \end{bmatrix}$$

$$C_{CM} = \begin{bmatrix} x & x & X \\ x & x & X \\ x & x & X \end{bmatrix}$$

The coefficient matrix $C_{ij}$ in equation (Eq. 1) can also be estimated using the partial least squares (PLS) method (instead of using equation Eq. 2).

Good estimation of the needed transformation matrices requires using a training data set that can cover the whole data space, i.e. the training data set must contain representative data samples for all possible variants of data samples that may be presented to the system or need to be processed by the system in the future (that is after completing the training faze). Preparing a good training data set is therefore essential to be able to proceed with this approach.

Figure 23:
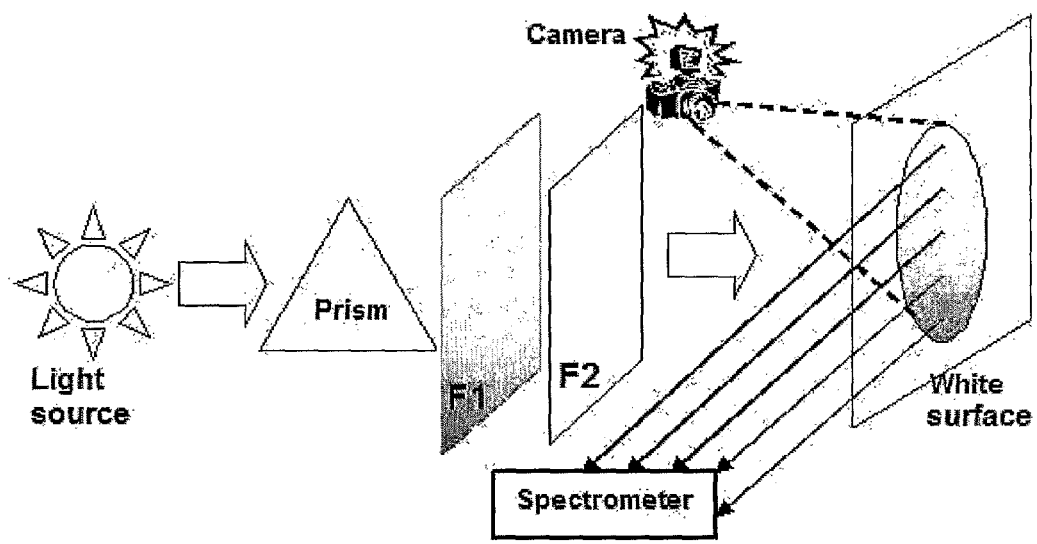
FIG. 23 is a schematic and simplified illustration of a set up for measuring the response of a specific multiple filter F2 to various colours (by generating rainbow light) as well as various light intensities (by using a variable transmission filter F1). The response signals are measured by using a conventional spectrometer and a conventional digital camera.
Figure 24:
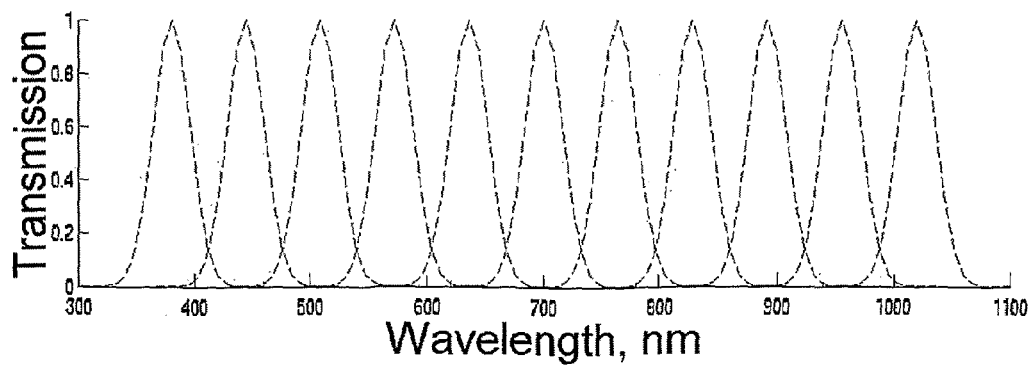
FIG. 24 is a schematic and simplified illustration of a set of 11 basis function vectors in the wavelength interval ranging from 300 nm up to 1100 nm.

FIG. 23 illustrates a set up for measuring a uniform-filter's response to a projected rainbow with varying light intensity. The rainbow is projected through a transmission-varying filter F1 (with smooth variation from 0 to 100%) so that various light intensities are obtained or generated of every colour of the rainbow. For instance, F1 affects the narrow almost-uniform red region of the rainbow, so that the colour of this region is gradually changed towards blackened red, i.e. a set of colours ranging from red to blackened red or black can be seen in this region of the rainbow. The same applies for the other rainbow uniform-colour regions. The uniform multiple filter of interest is represented by F2 in FIG. 23. The camera shown in the figure is a monochrome camera. However, it is also possible to use a colour camera if the multiple colour filter is built of the embedded camera colour mosaic and an external colour mosaic. Uniform colour filters of the same type as the external mosaic elements must be (interchangeably) used as F2 in FIG. 23.

The camera registers an image of a whole rainbow projected on a white surface (e.g. a white paper). The different parts in the set up, the light source, the prism, F1, the white surface, as well as the camera, must be kept constant during acquiring the whole training data set to be able to assume pixel-wise matching between the registered images. The pixel values are, in this case, the multiple filter responses required to build the training data set.

The present invention also relates to a method of performing spectral measurements with the use of an inventive arrangement. Depending on the used approach for transforming a multi-band image into a multi- or hyperspectral image, it is often necessary to measure the spectral characteristics of the utilised multiple colour filters, or to measure these filters' responses to various types of incident light. Measuring the spectral characteristics of multiple colour filters (uniform and mosaics) has been discussed previously. What will be discussed here is how a spectrometer (also called spectroradiometer) is used to measure spectra at different points or regions of the rainbow projected on a white surface, as illustrated by FIG. 23. However, it is better and also easier to perform the measurements through, for instance, holes made in this white surface. It is possible to use a plate of hard material containing holes or to simply use a suitable grid or net of hard material (to measure the spectra through these holes using a spectrometer), and covering it with a loosely placed white cover without holes (to project the rainbow upon and register an image of it using a camera).

Given N colour bands produced by multiple colour filters, with transmission curves TC that are products of the transmission curves of the constituent colour filters, it is possible to estimate approximate spectra by the approaches described below. Note that what an image sensor element registers is the incident energy (number of incoming light photons as a function of wavelength) x multiplied by the multiple filter's transmission curve (e.g. $t_1 \cdot t_2$ in case the multiple filter consists of two overlapping colour filters with the transmission curves $t_1$ and $t_2$) and the result is finally multiplied by the sensitivity curve $\sigma$ of the sensor element itself (fraction of energy absorbed by the sensor as a function of wavelength), as described by the following element-wise product of vectors:

$\sigma \cdot t_1 \cdot t_2 \cdot x$

However, $\sigma$ is considered equal to one for the sake of simplicity.

Several approaches using linear algebra for estimating approximate spectra at an image element will now be described.

The Statistical Approach Using the Partial Least Squares Method

Let x be the vector of the spectral signal (i.e. a spectrum vector with m elements), and y is the N-band output vector from N different multiple filters (an N elements vector). An efficient way of estimating spectra x from multi-band data y is to statistically estimate a linear relation P between x and y, such that $x = Py$ (Eq. 5)

using a training data set of Q known spectra x (measured by a conventional spectrometer) and Q corresponding image responses y (registered by a camera) for various types of incident light. The measured responses $y_i$, i=1, 2 ..., Q, may form a matrix Y with $y_i$ as columns, and analogously for the spectra $x_i$ forming matrix X (m×Q). Let the dimension of $y_i$ be D, and let the number Q of training pairs $(x_i, y_i)$ exceeds the dimension, Q>D, making the matrix Y non-standing (D×Q) rectangular. This may then be formulated as $X = PY$ (Eq. 6)

and may be solved by the partial least squares (PLS) method, yielding the estimate P' (m×D). Finally, estimates of x, denoted by x', are formed by $x' = P'y_j$, where $y_j$ are image responses outside the training data set, i.e. new measured image responses that are not included in the training data set.

Figure 25:
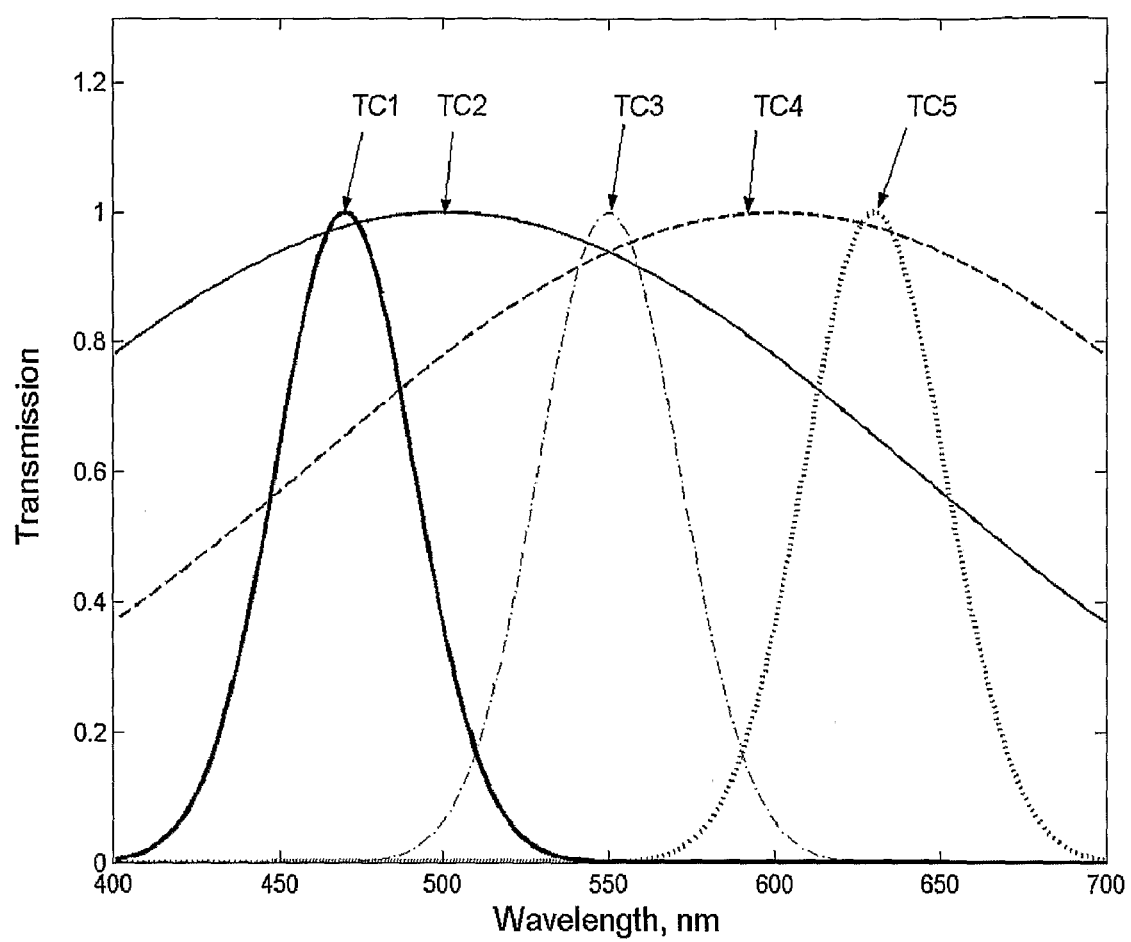
FIGS. 25, 26 and 27 are schematic and simplified illustrations showing some examples where two filters with overlapping transmission curves TC are used to approximate two or three filters with narrower curves TC.
Figure 26:
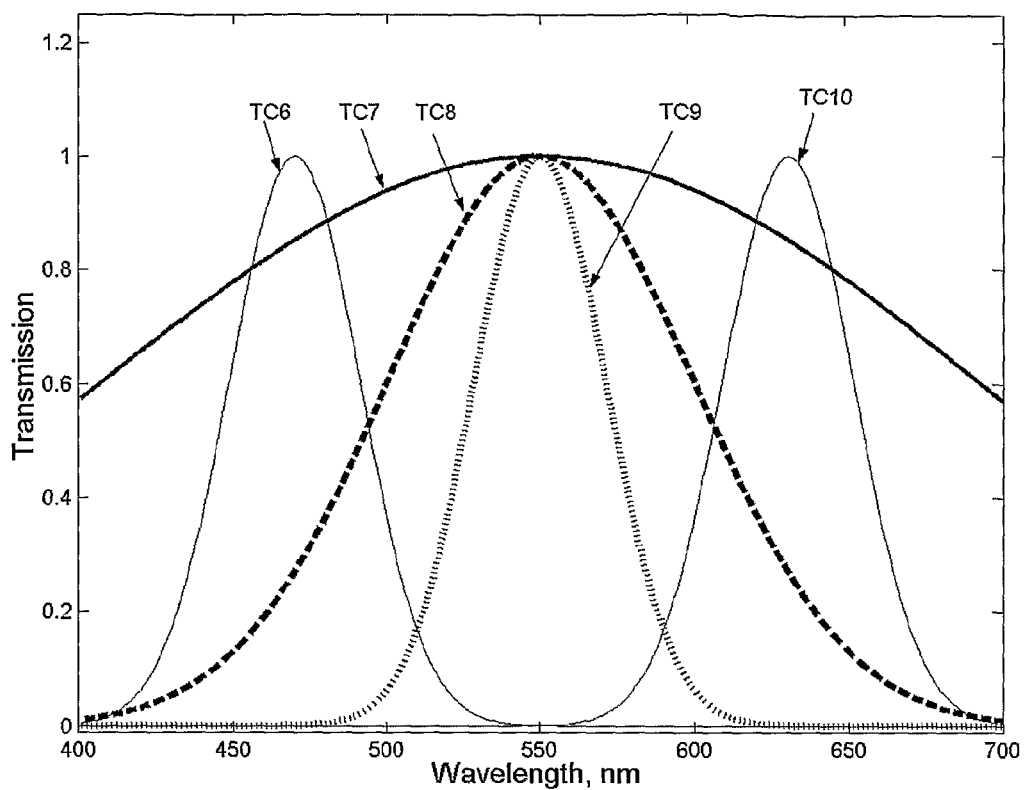
Figure 27:
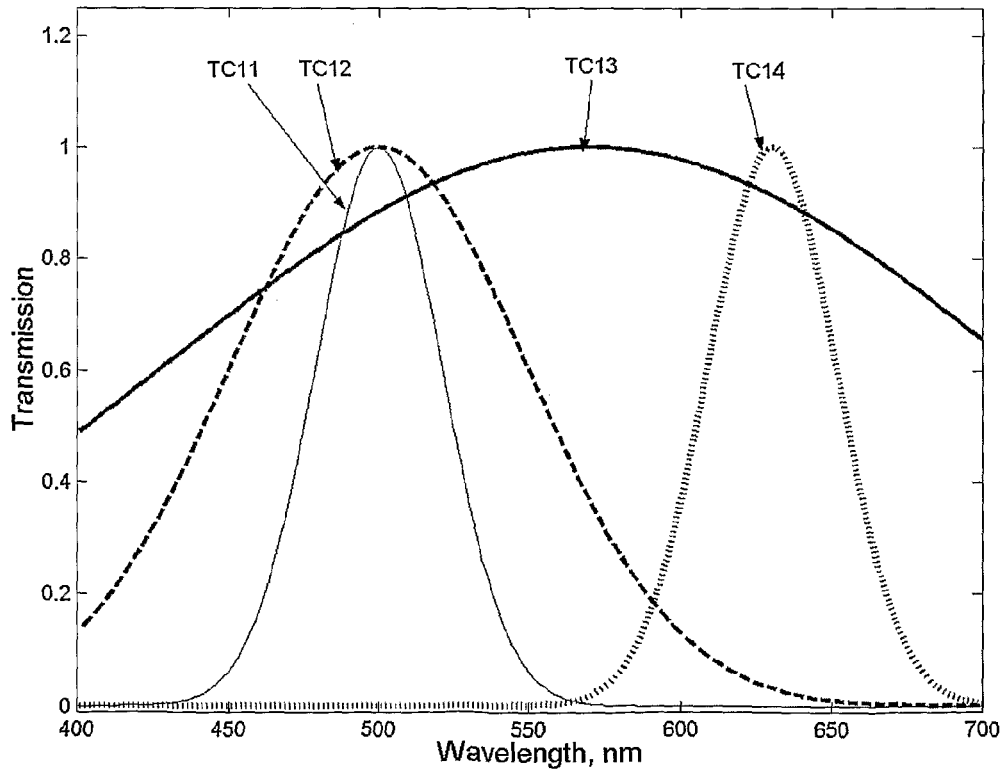

This approach can be seen as estimating approximates of narrow-band filters, using lower-cost broad-band filters. FIGS. 25, 26 and 27 show some examples where two filters with overlapping transmission curves TC are used to approximate a number of narrower filters. In FIG. 25, filters with the transmission curves TC2 and TC4 can be used to approximate filters with TC1, TC3 and TC5. FIG. 26 shows that filters with TC7 and TC8 can be used to approximate filters with TC6, TC9 and TC10. Finally, in FIG. 27, filters with TC12 and TC13 can be used to approximate filters with TC11 and TC14.

The Artificial Neural Networks Approach

Figure 33:
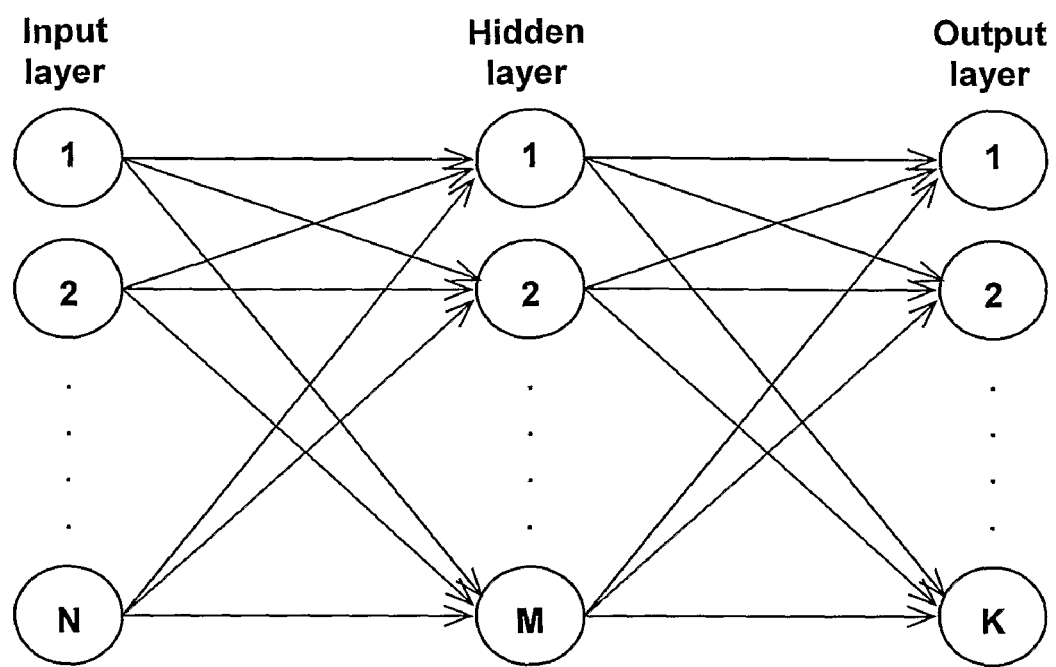
FIG. 33 shows a schematic illustration of a feed forward artificial neural network.

The interpolation approach 2 as well as the transformation-to-spectra approach 1 can be performed using artificial neural networks. FIG. 33 shows a feed-forward neural network with three layers (input, hidden and output) that can be used for both linear and non-linear function estimation. The input layer has N nodes, where N is the number of input parameters to be transformed into desired results which appear on the K output-layer nodes, where K is the number of the estimated parameters. The hidden layer contains M nodes, where M is selected to obtain the most cost effective model (usually M=N+1 is the best choice). Every input-node is connected to all hidden-layer nodes, each of which is in turn connected to all output nodes. All information moves in one direction during operation, from the input layer to the output layer. Each node in the hidden and the output layers has two parts, a linear summation function and a non-linear activation function as follows:

$$y = a \tanh\left(\sum_{i=1}^{j} w_i x_i + b\right) \quad \text{(Eq. 7)}$$

where y is the output of the node, a is a scaling factor, tanh is the hyperbolic tangent function, j is the number of inputs to the node, $x_i$ are the inputs to the node, $w_i$ are weighting factors related to each input connection to the node, and b is a bias factor. The factors a, b and $w_i$ are estimated by training the neural network using a training data set consisting of pairs of input and output parameters that the neural network will be used for (i.e. to estimate the desired output parameters when entering the input parameters to the network).

As an illustrating example, lets look at the case of transforming the responses of the multiple filters CR, CG, CB and C, into the responses of MR, MG, MB and M. Here it is computationally efficient to use a neural network with N=4 input nodes (receiving the CR, CG, CB and C signals), M=5 hidden nodes and K=4 output nodes (generating the MR, MG, MB and M signals).

When transforming multiple filter responses into spectra, the neural network should have as many inputs as the different multiple filters, e.g. 16 input nodes (and 17 hidden nodes) are required when using the multiple filter described in FIG. 6. The output layer has as many nodes as the number of the desired spectral bands in the estimated spectra.

Other Advantages and Applications

A multiple-filter-mosaic image, which is as small as a monochromatic image (i.e. a single-band image), can easily be transferred and saved, making this technique useful for airborne and satellite-borne imaging systems and the like, as well as telemedicine and electronic medical recording and archiving, where the acquired images are transferred to another place to be saved (and archived) and/or analysed (after generation of multi- or hyperspectral images). Demosaicking a multiple-filter-mosaic image generates a multi-band image which is also much smaller (and consequently easier to transfer and save) than a hyperspectral image. Systems with interchangeable uniform filters (using filter wheels or flat transmittive filters) directly generate multi-band images. A multi- or hyperspectral image can be generated and analysed when needed, by transforming the corresponding multi-band image.

Another important application where this invention can useful is to generate a multi- or hyperspectral image, then perform appropriate processing and analysis to compensate for the lighting and the surrounding environment effects on the image, and finally converting the processed multi- or hyperspectral image back into a colour RGB image. Efficient colour correction can be performed by this way. It is also possible to optimise (by choosing and using appropriate R, G and B filters) the resulting colour RGB image for a certain display, e.g. the currently used display device in the system.

Finally, it is of course possible to construct a spectrometer using the technology and methods described above. The main difference is that there is no need for interpolation/extrapolation to fill-in empty spaces in the extracted separate arrays belonging to the different multiple filters. What is needed to be done instead here is to simply compute the mean values of the non-empty elements of each separate array. The sums of non-empty array elements can be used (instead of the mean values) if the separate arrays contain the same number of non-empty elements. Hence, each separate array will generate a single scalar value. These scalar values form a single vector where these values are inserted according to a specific order. Thereafter, this multi-band vector can be transformed into a spectrum (using one of the transformation-to-spectra approaches described above) with as high spectral resolution and accuracy as possible.

Furthermore, it is also possible to construct a spectrometry device that can perform a number of spectral measurements in parallel, since the spatial resolution of the image sensor array is usually high enough to be used with a multiple filter mosaic consisting of a large number of repeated mosaic pattern units, which is the filter mosaic pattern that is repeated to form a mosaic covering the whole image sensor array. Therefore, different portions of the image sensor array, covered by at least one mosaic pattern unit, can be used to build independent spectrometers, as shown in FIG. 28 where we have a multiple filter mosaic consisting of four mosaic units of the type (i.e. the same multiple filter mosaic pattern) presented in FIG. 6. In FIG. 28 it is possible to use each of the four mosaic units to build an independent spectrometer if it is possible to deliver four different light signals, in parallel, to these mosaic unit areas, which can be easily achieved by using four separate optical fibres OF, each of which delivers light to a different mosaic unit. However, in the cases where pixel-wise matching, between the image sensor array and the multiple filter mosaic, is not possible, it is important to assure that the optical fibre OF covers at least one mosaic unit. It is also possible to use a lens system (as described by the FIGS. 3, 11-16 and 21) to build a multi- or hyperspectral camera (that can generate multi- or hyperspectral images with spectra in the pixels), or to build a spectrometer (that generates one single spectrum), using an image sensor array with spatial resolution and number of elements that is enough to leave out at least one portion of the sensor array, i.e. these portions are not used in building the camera or the spectrometer, each of which is covered (by direct physical contact, or by placing the colour mosaics in the optical path OF as discussed previously) by at least one multiple mosaic unit, to be covered by an optical fibre OF and build a separate spectrometer.

Figure 29:
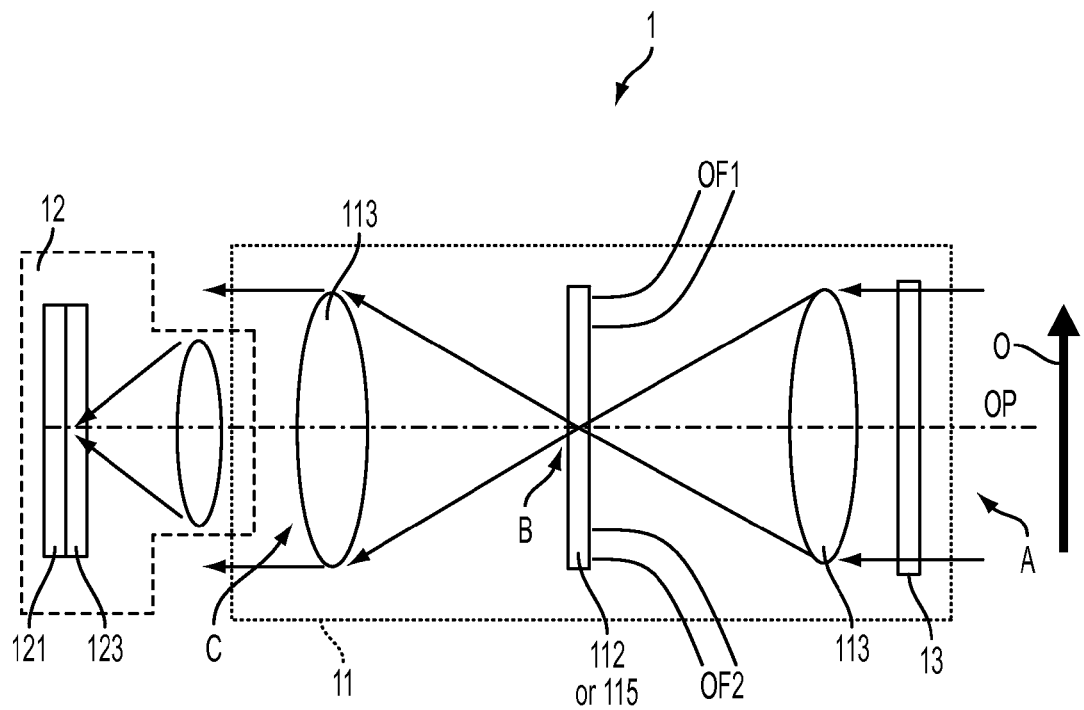
FIGS. 29 and 30 are schematic and simplified illustrations of modified versions of the embodiments presented in FIGS. 11 and 13. The new embodiments register a multi- or hyperspectral image or measure a spectrum of the object O, and at the same time measure spectra of light signals fed by using the optical fibres OF1 and OF2.
Figure 30:
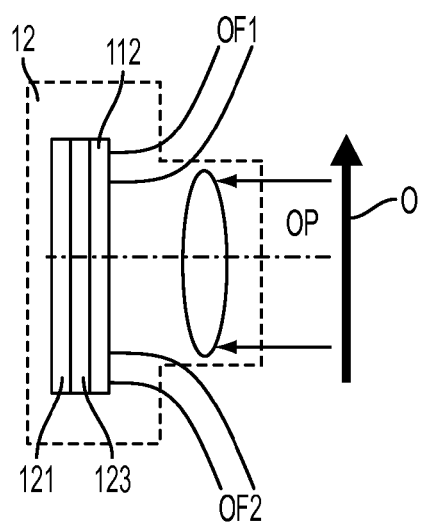

FIGS. 29 and 30 show how the embodiments shown in FIGS. 11 and 13, respectively, can be modified to build multiple devices. In FIG. 29 it is possible to register a multi- or hyperspectral image or measure a spectrum of the object O, and at the same time measure spectra of light signals fed by using the optical fibres OF1 and OF2. At least one optical fibre OF is needed to be able to compensate for the lighting and surrounding environment impact on the measured spectrum or the registered multi- or hyperspectral image, e.g. colour correction can be then easily performed.

Figure 31:
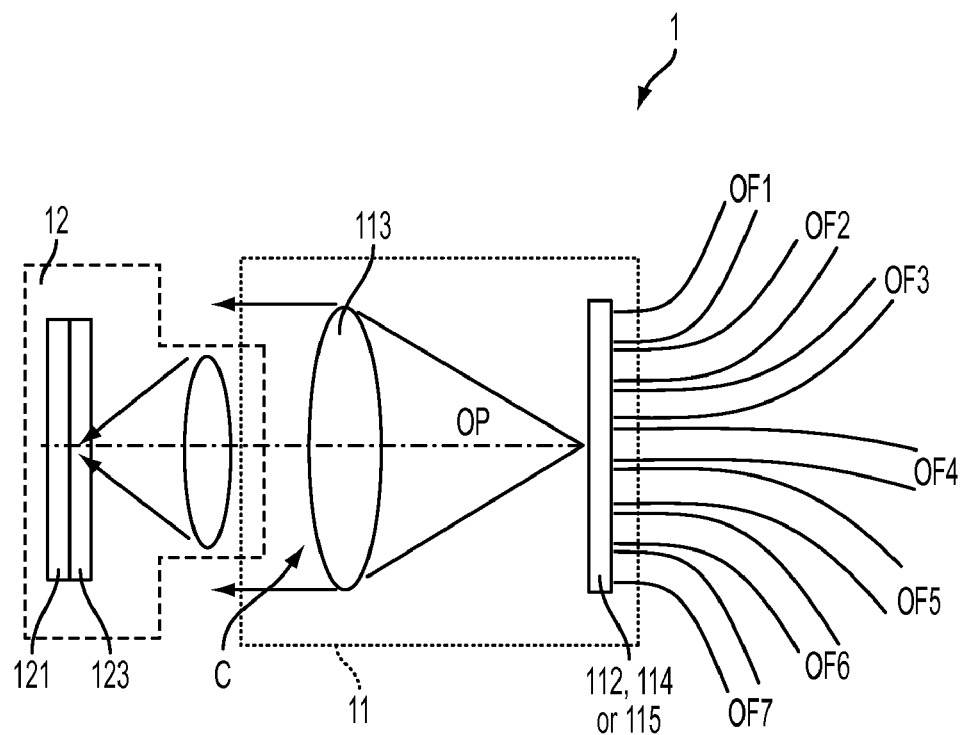
FIGs. 31 and 32 are schematic and simplified illustrations of two embodiments (that correspond to the embodiments in FIGS. 29 and 30, respectively) where only optical fibres OF are used to provide light signals to the multiple filter mosaics in the arrangement.
Figure 32:
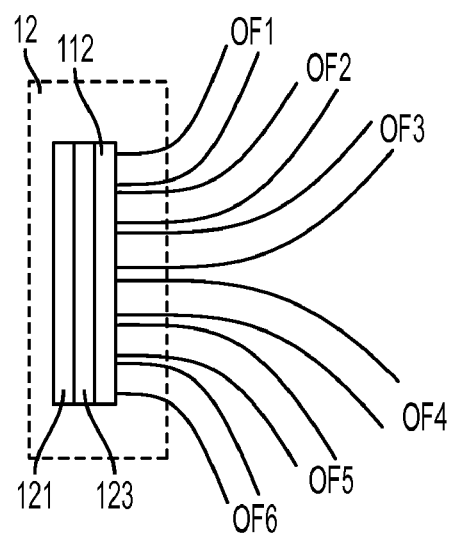

FIGS. 31 and 32 show two embodiments (that correspond to the embodiments in FIGS. 29 and 30, respectively) where only optical fibres OF are used to provide light signals to the multiple filter mosaics in the arrangement. At least one optical fibre OF is used, but if the application demands, it is also possible to use up to as many optical fibres OF as the number of the image sensor array elements, and to distribute them uniformly over the image sensor array area. Element wise matching between the single optical fibres OF and the image sensor elements or the multiple filter elements is preferred.

It will be understood that the invention is not restricted to the aforedescribed and illustrated exemplifying embodiments thereof and that modifications can be made within the scope of the inventive concept as illustrated in the accompanying claims. Hexagonal, octagonal or other pixel arrangement pattern can analogously be used instead of the currently widely-used rectangular grid arrangement in image sensors. The "Super CCD" produced by announced by Fujifilm (Fujifilm, 2004, News Highlights—New 4th Generation Super CCD Producing higher resolution and wider dynamic range by sophisticated miniaturization technologies, Fujifilm website; available from World Wide Web @ http://home.fujifilm.com/news/n030122.html, cited September 2005).

The invention claimed is:

1. An arrangement for the production of instantaneous or non-instantaneous multi-band images, comprising: light collecting means, an image sensor with at least one two dimensional sensor array with an instantaneous colour separating means, positioned before or embedded in said two dimensional sensor array in the optical path of said arrangement, and a first uniform spectral filter in said optical path, with the purpose of restricting imaging to certain parts of the electromagnetic spectrum, characterised in that a filter unit is used comprising overlapping colour or spectral filter mosaics, or a filter unit comprising overlapping colour or spectral filter mosaics and uniform colour or spectral filters, that said filter unit is either permanently or interchangeably positioned before said colour separating means in said optical path in, or close to, converged light, that said colour or spectral filter mosaics comprises a multitude of homogeneous filtering regions, where there is an overlap or partial overlap between transmission curves of said filtering regions of colour or spectral filter mosaics, said uniform colour or spectral filters and the filtering regions of said colour separating means, that said transmission curves of said colour or spectral filter mosaics, said uniform filters and said colour separating means are spread out in the intervals of a spectrum to be studied, and that the combination of said colour separating means and said colour or spectral filter mosaics produces different sets of linearly independent transmission curves, and that the multiple-filter image captured by said image sensor is demosaicked, by identifying and segmenting the image regions that are affected by the regions of the multiple filter mosaic, to obtain a multi-band image, and that said multi-band image is transformed by using one of the two approaches, the statistical approach using a partial least squares method or an artificial neural network approach, to obtain a multi- or hyperspectral image.

2. An arrangement according to claim 1, characterised in that said image sensor comprises three separate two dimensional sensor arrays, and that said colour separating means comprises means for separating incoming light into three different spectral bands, one band to respective two dimensional sensor array, such as a beam splitter with three separate uniform colour filters or a colour separating beam splitter, and that said filter unit comprises colour or spectral filter mosaics.

3. An arrangement according to claim 1, characterised in that at least one additional optical fibre is used to provide light signal to a portion of the multiple filter mosaic in said arrangement, while the rest of said multiple filter mosaic area receives light signals delivered by a lens system.

4. A system comprising an arrangement according to claim 3, characterised in that the multiple-filter image captured by said image sensor is demosaicked by identifying and segmenting the image regions that are affected by the regions of the multiple filter mosaic, and that the mean values are calculated for the image regions, detecting the optical fibres' light-signals, to generate one multi-band mean-vector for each region, while interpolation is performed on the other image regions by using one of the three approaches, the interpolation approach using distance transform, the interpolation approach using statistical transformation employing the partial least squares method, or the artificial neural network approach, to obtain a multi-band image with complete band-content in these image regions, and that said multi-band image, including said multi-band mean-vectors, is transformed by using one of the two approaches, the statistical approach using the partial least squares method or the artificial neural network approach, to obtain a multi- or hyperspectral image, and a spectrum corresponding to each said multi-band mean-vector.

5. A system comprising an arrangement according to claim 4, characterised in that at least one of the optical fibres delivers the lighting source's signal and the resulting said multi-band mean-vector and the corresponding estimated spectrum are used to compensate for the lighting effect on said multi-band image and said multi- or hyperspectral image, respectively, and by this way, reflectance spectral responses, respectively, reflectance spectra are obtained in the pixels.

6. A system comprising an arrangement according to claim 5, characterised in that said reflectance spectral responses and said reflectance spectra are converted into R, G and B values to generate a colour corrected image by using R, G and B filters with desired or optimised transmission curves.

7. An arrangement according to claim 1, characterised in that at a number of optical fibres is used to provide light signals to said multiple filter mosaic in said arrangement.

8. An arrangement according to claim 1, characterised in that each said two dimensional sensor array comprises layered photodiodes with at least three layers, so that spectral or colour separation is embedded into said sensor array and no additional colour separating means (123, 123a, 123b, 123c or 123d, respectively) is needed.

9. An arrangement according to claim 8, characterised in that a CMYT or a CMY colour mosaic is used to achieve the desired multiple filtering effect, or that uniform C, M and Y colour filters are used to achieve the desired multiple filtering effect, that the used layered photodiodes have at least three layers, and that pixel-wise matching is preferred between said image sensor array and said colour mosaic.

10. An arrangement according to claim 8, characterised in that a CMYTBrBk colour mosaic is used to achieve the desired multiple filtering effect, when using layered photodiodes with at least three layers.

11. An arrangement according to claim 8, characterised in that a CMYT or a CMYTBk colour mosaic is used to achieve the desired multiple filtering effect, when using layered photodiodes with at least three layers where at least one of the layers is sensitive to near infrared light and at least another one of the layers is sensitive to near ultraviolet light.

12. An arrangement according to claim 1, characterised in that said colour or spectral filter mosaics and/or said uniform colour or spectral filters are produced by existing colour laser or ink printing techniques, or by other photographic printing techniques, on transparent or semitransparent materials.

13. An arrangement according to claim 1, characterised in that said image sensor comprises one sole two dimensional sensor array, and a colour separating means that is a second colour or spectral filter mosaic with elements fitting individual pixel elements on said sole two dimensional sensor array.

14. An arrangement according to claim 1, characterised in that a digital camera is a part of said arrangement, and that said image sensor and said colour separating means are parts of said digital camera.

15. An optical auxiliary device, adapted to be connected to a conventional digital camera, with or without own camera lens, in a manner to align the optical axis of said optical device with the optical axis of said digital camera, characterised in that said optical device and said camera form an arrangement according to claim 1 when connected to each other.

16. A colour or spectral mosaic comprising at least one first colour or spectral filter mosaic, characterised in that said colour or spectral mosaic is adapted to be inserted into an ocular, whereby said ocular and inserted said colour or spectral mosaic in combination with a conventional digital camera forms an arrangement according to claim 1.

17. A colour or spectral mosaic according to claim 16, characterised in that said colour or spectral mosaic is adapted to be inserted into a ocular, such as a telescope or a microscope.

18. An arrangement according to claim 1, characterised in that the sets of uniform multiple filters or multiple filter mosaics are generated by combining complementary colour or spectral filter mosaics and/or uniform colour or spectral filters, such as RGBT or RGB and CMYT or CMY colour mosaics, or uniform colour filters of these colours, and that pixel-wise matching is preferred between said image sensor array and said multiple filter mosaic.

19. An arrangement according to claim 18, characterised in that a VT mosaic is placed in converged light to contribute to building the resulting multiple filter mosaic.

20. An arrangement according to claim 1, characterised in that an RGB and a CMYTBrBk colour mosaics are combined to build the resulting multiple filter mosaic.

21. An arrangement according to claim 1, characterised in that an RGCYBrBk and a VT colour or spectral mosaics are combined to build the resulting multiple filter mosaic.

22. A system comprising an arrangement according to any one of claims 1 to 6, characterised in that the multiple-filter image captured by said image sensor is demosaicked by identifying and segmenting the image regions that are affected by the regions of the multiple filter mosaic, and that interpolation is performed by using one of the three approaches, the interpolation approach using distance transform, the interpolation approach using statistical transformation employing the partial least squares method, or the artificial neural network approach, to obtain a multi-band image with complete bands, and that said multi-band image is transformed by using one of the two approaches, the statistical approach using the partial least squares method or the artificial neural network approach, to obtain a multi- or hyperspectral image.

23. A system comprising an arrangement according to any one of claims 1 to 9, characterised in that the multiple-filter image captured by said image sensor is demosaicked by identifying and segmenting the image regions that are affected by the regions of the multiple filter mosaic, and that the mean values are calculated for certain image regions generating one multi-band mean-vector for each region, while interpolation is performed on the other image regions by using one of the three approaches, the interpolation approach using distance transform, the interpolation approach using statistical transformation employing the partial least squares method, or the artificial neural network approach, to obtain a multi-band image with complete band-content in these image regions, and that said multi-band image, including said multi-band mean-vectors, is transformed by using one of the two approaches, the statistical approach using the partial least squares method or the artificial neural network approach, to obtain a multi- or hyperspectral image, and a spectrum corresponding to each said multi-band mean-vector.

24. An arrangement for the production of instantaneous or non-instantaneous multi-band images, comprising light: collecting means, an image sensor with at least one two dimensional sensor array with an instantaneous colour separating means, positioned before or embedded in said two dimensional sensor array in the optical path of said arrangement, and a first uniform spectral filter in said optical path, with the purpose of restricting imaging to certain parts of the electromagnetic spectrum, characterised in that a filter unit is used comprising overlapping colour or spectral filter mosaics and uniform colour or spectral filters, or a comprising overlapping uniform colour or spectral filters, such that said uniform colour or spectral filters are mounted on filter wheels or displayed by transmissive displays, that said filter unit is positioned before said colour separating means in said optical path in, or close to, converged light, that said colour or spectral filter mosaics comprises a multitude of homogeneous filtering regions, where there is an overlap or partial overlap between transmission curves of said filtering regions of colour or spectral filter mosaics, said uniform filters and the filtering regions of said colour separating means, that said transmission curves of said colour or spectral filter mosaics, said uniform colour or spectral filters and said colour separating means are spread out in the intervals of a spectrum to be studied, and that the combination of said colour separating means and said colour or spectral filter mosaics produces different sets of linearly independent transmission curves, and that the multiple-filter image captured by said image sensor is demosaicked, by identifying and segmenting the image regions that are affected by the regions of the multiple filter mosaic, to obtain a multi-band image, and that said multi-band image is transformed by using one of the two approaches, the statistical approach using a partial least squares method or an artificial neural network approach, to obtain a multi- or hyperspectral image.

25. An image sensor for the production of instantaneous multi-band images, comprising: at least one two dimensional sensor array, and an instantaneous colour separating means comprises a RGBT colour mosaic or a CMYT colour mosaic, embedded in said image sensor array, and a filter unit, characterised in that said image sensor comprises a colour or spectral filter mosaic, and that said filter unit can either be placed directly over said colour separating means, or integrated with said colour separating means, and that the image captured by said image sensor is demosaicked, by identifying and segmenting the image regions that are affected by the regions of the multiple filter mosaic, to obtain a multi-band image, and that said multi-band image is transformed by using one of the two approaches, the statistical approach using a partial least squares method or an artificial neural network approach, to obtain a multi- or hyperspectral image, and that said colour separating means comprises an RGBT colour mosaic while the said colour or spectral filter mosaic comprises an CMYT colour mosaic, or that said colour separating means comprises an CMYT colour mosaic while the said colour or spectral filter mosaic comprises an RGBT colour mosaic.

26. An arrangement according to claim 25, characterised in that said image sensor comprises three separate two dimensional sensor arrays with embedded colour filter mosaics, and that said colour separating means (122') comprises means for separating incoming light into three different spectral bands, one band to respective two dimensional sensor array, such as a beam splitter with three separate uniform colour or spectral filters (125a, 125b, 125c) or a colour separating beam splitter.

27. An arrangement according to claim 26, characterised in that said image sensor comprises four separate two dimensional sensor arrays (121a, 121b, 121c, 121d), where said sensor array (121d) is covered by an instantaneous colour separating means (123d) without using any uniform colour or spectral filter for said sensor array (121d).

* * * * *